(12) United States Patent
Ritland

(10) Patent No.: US 7,753,939 B2
(45) Date of Patent: Jul. 13, 2010

(54) POLYAXIAL CONNECTION DEVICE AND METHOD

(76) Inventor: Stephen Ritland, P.O. Box 2310, Flagstaff, AZ (US) 86003-2310

( * ) Notice: Subject to any disclaimer, the term of this patent is extended or adjusted under 35 U.S.C. 154(b) by 935 days.

(21) Appl. No.: 10/776,094

(22) Filed: Feb. 10, 2004

(65) Prior Publication Data

US 2004/0172023 A1 Sep. 2, 2004

Related U.S. Application Data

(62) Division of application No. 09/898,478, filed on Jul. 2, 2001, now Pat. No. 6,736,816.

(60) Provisional application No. 60/215,602, filed on Jun. 30, 2000.

(51) Int. Cl.
*A61B 17/70* (2006.01)
(52) U.S. Cl. .................. 606/264; 606/266; 606/276
(58) Field of Classification Search .................. 606/61, 606/72, 73, 264, 266, 276, 250, 307
See application file for complete search history.

(56) References Cited

U.S. PATENT DOCUMENTS

| | | |
|---|---|---|
| 2,191 A | 7/1841 | Pitney |
| 569,839 A | 10/1896 | Roeloffs |
| 605,652 A | 6/1898 | Pitt |
| 1,090,746 A | 3/1914 | Nourse |
| 1,097,978 A | 5/1914 | Johnson |
| 3,467,079 A | 9/1969 | James |
| 3,470,872 A | 10/1969 | Grieshaber |
| 3,875,595 A | 4/1975 | Froning |
| 3,893,454 A | 7/1975 | Hagelin |
| 4,041,939 A | 8/1977 | Hall .................. 606/61 |
| 4,232,660 A | 11/1980 | Coles |
| 4,440,168 A | 4/1984 | Warren |
| 4,481,947 A | 11/1984 | Chester |
| 4,545,374 A | 10/1985 | Jacobson |
| 4,573,448 A | 3/1986 | Kambin |
| 4,617,922 A | 10/1986 | Griggs |
| 4,620,460 A | 11/1986 | Gonzales, Jr. |
| 4,686,972 A | 8/1987 | Kurland |
| 4,736,738 A | 4/1988 | Lipovsek |
| 4,743,260 A | 5/1988 | Burton .................. 623/17 |
| 4,747,394 A | 5/1988 | Watanabe |
| 4,798,111 A | 1/1989 | Cheeseman |
| 4,803,976 A | 2/1989 | Frigg |

(Continued)

FOREIGN PATENT DOCUMENTS

CA 2320821 8/1999

(Continued)

OTHER PUBLICATIONS

U.S. Appl. No. 10/788,172, filed Feb. 25, 2004, Ritland.

(Continued)

*Primary Examiner*—Pedro Philogene
(74) *Attorney, Agent, or Firm*—Holme Roberts & Owen LLP

(57) ABSTRACT

A surgical implant assembly, and components thereof, are disclosed. Such assemblies include a connector device and an anchoring shaft. The assemblies are useful for insertion into bone and connecting a foreign object to bone via a polyaxial coupling mechanism.

20 Claims, 18 Drawing Sheets

U.S. PATENT DOCUMENTS

| | | | |
|---|---|---|---|
| 4,817,587 A | 4/1989 | Janese | |
| 4,862,891 A | 9/1989 | Smith | |
| 4,863,423 A | 9/1989 | Wallace | |
| 4,882,958 A | 11/1989 | McNeely | |
| 4,889,112 A | 12/1989 | Schachner et al. | |
| 4,946,458 A | 8/1990 | Harms et al. | |
| 4,995,875 A | 2/1991 | Coes | |
| 5,002,542 A | 3/1991 | Frigg | |
| 5,002,576 A | 3/1991 | Fuhrmann et al. | 623/17 |
| 5,018,507 A | 5/1991 | Montaldi | |
| 5,024,213 A | 6/1991 | Asher et al. | |
| 5,026,373 A | 6/1991 | Ray et al. | 606/61 |
| 5,030,220 A | 7/1991 | Howland | 606/61 |
| 5,030,223 A | 7/1991 | Anderson et al. | |
| 5,035,232 A | 7/1991 | Lutze et al. | |
| 5,048,379 A | 9/1991 | Gramera | |
| 5,052,373 A | 10/1991 | Michelson | |
| 5,055,104 A | 10/1991 | Ray | 606/61 |
| 5,084,043 A | 1/1992 | Hertzmann | |
| 5,098,435 A | 3/1992 | Stednitz | |
| 5,106,376 A | 4/1992 | Mononen | |
| 5,129,899 A | 7/1992 | Small et al. | |
| 5,129,900 A | 7/1992 | Asher et al. | 606/61 |
| 5,133,720 A | 7/1992 | Greenberg | |
| 5,135,525 A | 8/1992 | Biscoping | |
| 5,148,724 A | 9/1992 | Rexford | |
| 5,158,543 A | 10/1992 | Lazarus | |
| 5,165,306 A | 11/1992 | Hellon | |
| 5,195,541 A | 3/1993 | Obenchain | |
| 5,217,007 A | 6/1993 | Ciaglia | |
| 5,275,600 A | 1/1994 | Allard et al. | |
| 5,275,611 A | 1/1994 | Behl | |
| 5,279,567 A | 1/1994 | Ciaglia | |
| 5,292,309 A | 3/1994 | Van Tassel | |
| 5,303,694 A | 4/1994 | Mikhail | |
| 5,304,179 A | 4/1994 | Wagner | |
| 5,306,275 A | 4/1994 | Bryan | |
| 5,306,309 A | 4/1994 | Wagner et al. | 623/17 |
| 5,312,360 A | 5/1994 | Behl | |
| 5,312,405 A | 5/1994 | Korotko et al. | 606/61 |
| 5,330,473 A | 7/1994 | Howland | |
| 5,330,474 A | 7/1994 | Lin | |
| 5,330,476 A | 7/1994 | Hiot et al. | |
| 5,356,413 A | 10/1994 | Martins et al. | |
| 5,363,841 A | 11/1994 | Coker | |
| 5,415,661 A | 5/1995 | Holmes | 606/69 |
| 5,431,639 A | 7/1995 | Shaw | |
| 5,431,651 A | 7/1995 | Goble | |
| D361,381 S | 8/1995 | Koros et al. | |
| 5,439,464 A | 8/1995 | Shapiro | |
| 5,466,238 A | 11/1995 | Lin | 606/61 |
| 5,472,426 A | 12/1995 | Bonati | |
| 5,474,555 A | 12/1995 | Puno et al. | 606/73 |
| 5,480,401 A | 1/1996 | Navas | |
| 5,484,440 A | 1/1996 | Allard | 606/73 |
| 5,489,274 A | 2/1996 | Chu | |
| 5,489,308 A | 2/1996 | Kuslich et al. | 623/17 |
| 5,498,262 A | 3/1996 | Bryan | |
| 5,499,983 A | 3/1996 | Hughes | |
| 5,501,684 A | 3/1996 | Schlapfer et al. | |
| 5,512,038 A | 4/1996 | O'Neal et al. | |
| 5,545,166 A | 8/1996 | Howland | |
| 5,549,612 A | 8/1996 | Yapp et al. | |
| 5,558,622 A | 9/1996 | Greenberg | |
| 5,562,663 A | 10/1996 | Wisnewski et al. | |
| 5,565,502 A | 10/1996 | Glimcher et al. | 523/115 |
| 5,569,300 A | 10/1996 | Redmon | |
| 5,584,831 A | 12/1996 | McKay | |
| 5,584,833 A | 12/1996 | Fournet-Fayard et al. | |
| 5,591,166 A | 1/1997 | Bernhardt et al. | 606/61 |
| 5,591,235 A | 1/1997 | Kuslich | 606/61 |
| 5,593,409 A | 1/1997 | Michelson | 606/61 |
| 5,601,550 A | 2/1997 | Esser | |
| 5,603,714 A * | 2/1997 | Kaneda et al. | 606/61 |
| 5,611,778 A | 3/1997 | Brinon | |
| 5,613,968 A | 3/1997 | Lin | |
| 5,628,740 A * | 5/1997 | Mullane | 606/61 |
| 5,643,263 A | 7/1997 | Simonson | 606/61 |
| 5,643,264 A | 7/1997 | Sherman et al. | 606/61 |
| 5,645,544 A | 7/1997 | Tai et al. | |
| 5,645,599 A | 7/1997 | Samani | 623/17 |
| 5,667,506 A | 9/1997 | Sutterlin | |
| 5,683,392 A | 11/1997 | Richelsoph et al. | |
| 5,683,463 A | 11/1997 | Godefroy et al. | 623/17 |
| 5,687,739 A | 11/1997 | McPherson | |
| 5,690,632 A | 11/1997 | Schwartz et al. | 606/73 |
| 5,691,397 A | 11/1997 | Glimcher et al. | 523/115 |
| 5,695,993 A | 12/1997 | Fukudome | |
| 5,702,455 A | 12/1997 | Saggar | 623/17 |
| 5,716,355 A | 2/1998 | Jackson et al. | |
| 5,716,415 A | 2/1998 | Steffee | 623/17 |
| 5,725,528 A | 3/1998 | Errico et al. | 606/61 |
| 5,735,850 A | 4/1998 | Baumgartner et al. | |
| 5,735,851 A * | 4/1998 | Errico et al. | 606/61 |
| 5,735,899 A | 4/1998 | Schwartz et al. | 623/17 |
| 5,743,853 A | 4/1998 | Lauderdale | |
| 5,746,720 A | 5/1998 | Stouder, Jr. | |
| 5,746,741 A | 5/1998 | Kraus et al. | 606/54 |
| 5,752,957 A | 5/1998 | Ralph et al. | 606/61 |
| 5,766,221 A | 6/1998 | Benderev et al. | |
| 5,766,253 A | 6/1998 | Brosnahan, III | 623/17 |
| 5,772,582 A | 6/1998 | Huttner et al. | |
| 5,782,832 A | 7/1998 | Larsen et al. | 606/61 |
| 5,785,648 A | 7/1998 | Min | |
| 5,785,710 A | 7/1998 | Michelson | 606/61 |
| 5,785,712 A | 7/1998 | Runciman et al. | |
| 5,792,044 A | 8/1998 | Foley | |
| 5,797,912 A | 8/1998 | Runciman et al. | |
| 5,800,435 A * | 9/1998 | Errico et al. | 606/61 |
| 5,810,816 A | 9/1998 | Roussouly et al. | |
| 5,810,817 A | 9/1998 | Roussouly et al. | |
| D399,955 S | 10/1998 | Koros et al. | |
| 5,816,257 A | 10/1998 | Chin | |
| 5,827,328 A | 10/1998 | Buttermann | 623/17 |
| 5,836,948 A | 11/1998 | Zucherman et al. | 606/61 |
| RE36,020 E | 12/1998 | Moore et al. | |
| 5,851,207 A | 12/1998 | Cesarone | |
| 5,860,977 A | 1/1999 | Zucherman et al. | 606/61 |
| 5,865,847 A | 2/1999 | Kohrs et al. | 623/17 |
| 5,865,848 A | 2/1999 | Baker | 623/17 |
| 5,876,404 A | 3/1999 | Zucherman et al. | 606/61 |
| 5,882,344 A | 3/1999 | Stouder, Jr. | |
| 5,885,285 A | 3/1999 | Simonson | 606/61 |
| 5,885,299 A | 3/1999 | Winslow et al. | |
| 5,885,300 A | 3/1999 | Tokuhashi et al. | |
| 5,891,147 A | 4/1999 | Moskovitz et al. | |
| 5,895,352 A | 4/1999 | Kleiner | |
| 5,895,390 A | 4/1999 | Moran et al. | |
| 5,897,593 A | 4/1999 | Kohrs et al. | 623/17 |
| 5,899,901 A | 5/1999 | Middleton | |
| 5,902,231 A | 5/1999 | Foley | |
| 5,902,304 A | 5/1999 | Walker et al. | |
| 5,904,650 A | 5/1999 | Wells | |
| 5,906,616 A | 5/1999 | Pavlov et al. | 606/61 |
| 5,913,818 A | 6/1999 | Co et al. | |
| 5,928,139 A | 7/1999 | Koros | |
| 5,928,233 A | 7/1999 | Apfelbaum et al. | 606/61 |
| 5,931,838 A | 8/1999 | Vito | |
| 5,938,663 A | 8/1999 | Petreto | |
| 5,944,658 A | 8/1999 | Koros et al. | |
| 5,947,965 A | 9/1999 | Bryan | |
| 5,954,635 A | 9/1999 | Foley | |
| 5,954,671 A | 9/1999 | O'Neil | |
| 5,961,516 A | 10/1999 | Graf | |

| | | | |
|---|---|---|---|
| 5,967,970 A | 10/1999 | Cowan | |
| 5,968,098 A | 10/1999 | Winslow | 623/17 |
| 5,971,920 A | 10/1999 | Nagel | |
| 5,976,135 A | 11/1999 | Sherman et al. | |
| 5,976,146 A | 11/1999 | Ogawa | |
| 5,984,924 A | 11/1999 | Asher et al. | 606/61 |
| 5,996,447 A | 12/1999 | Bayouth | |
| 5,997,539 A | 12/1999 | Errico et al. | 606/61 |
| 6,004,322 A | 12/1999 | Bernstein | |
| 6,007,487 A | 12/1999 | Foley et al. | |
| 6,010,520 A | 1/2000 | Pattison | |
| 6,017,342 A | 1/2000 | Rinner | |
| 6,027,533 A | 2/2000 | Olerud | |
| 6,045,579 A | 4/2000 | Hochshuler et al. | 623/17 |
| 6,048,342 A | 4/2000 | Zucherman et al. | 606/61 |
| 6,050,997 A * | 4/2000 | Mullane | 606/61 |
| 6,063,088 A | 5/2000 | Winslow | 606/61 |
| 6,068,630 A | 5/2000 | Zucherman et al. | 606/61 |
| 6,074,390 A | 6/2000 | Zucherman et al. | 606/61 |
| 6,074,393 A * | 6/2000 | Sitoto | 606/73 |
| 6,080,155 A | 6/2000 | Michelson | |
| 6,080,193 A | 6/2000 | Hochshuler et al. | 623/17 |
| 6,081,741 A | 6/2000 | Hollis | |
| 6,083,225 A | 7/2000 | Winslow et al. | 606/61 |
| 6,083,226 A | 7/2000 | Fiz | |
| 6,090,112 A | 7/2000 | Zucherman et al. | 606/61 |
| 6,102,948 A | 8/2000 | Brosnahan, III | 623/17 |
| 6,113,602 A | 9/2000 | Sand | 606/61 |
| 6,117,137 A | 9/2000 | Halm et al. | 606/72 |
| 6,117,174 A | 9/2000 | Nolan | 623/17.11 |
| 6,120,434 A | 9/2000 | Kimura | |
| 6,120,506 A | 9/2000 | Kohrs et al. | 606/80 |
| 6,123,705 A | 9/2000 | Michelson | 606/61 |
| 6,123,706 A | 9/2000 | Lange | 606/61 |
| 6,132,430 A | 10/2000 | Wagner | 606/61 |
| D433,296 S | 11/2000 | Yamakawa | |
| 6,146,383 A | 11/2000 | Studer et al. | |
| 6,149,652 A | 11/2000 | Zucherman et al. | 606/61 |
| 6,149,686 A | 11/2000 | Kuslich et al. | 623/17.11 |
| 6,152,871 A | 11/2000 | Foley | |
| 6,152,926 A | 11/2000 | Zucherman et al. | 606/61 |
| 6,156,006 A | 12/2000 | Brosens | |
| 6,156,038 A | 12/2000 | Zucherman et al. | 606/61 |
| 6,159,179 A | 12/2000 | Simonson | |
| 6,162,170 A | 12/2000 | Foley | |
| 6,162,236 A | 12/2000 | Osada | |
| D436,513 S | 1/2001 | Yamakawa | |
| 6,176,823 B1 | 1/2001 | Foley | |
| 6,176,861 B1 | 1/2001 | Bernstein et al. | |
| 6,179,838 B1 | 1/2001 | Fiz | 606/61 |
| D438,074 S | 2/2001 | Marr | |
| 6,183,471 B1 | 2/2001 | Zucherman et al. | 606/61 |
| 6,187,005 B1 | 2/2001 | Brace et al. | |
| 6,190,387 B1 | 2/2001 | Zucherman et al. | 606/61 |
| 6,190,414 B1 | 2/2001 | Young et al. | 623/17.15 |
| 6,196,969 B1 | 3/2001 | Bester et al. | |
| 6,197,002 B1 | 3/2001 | Peterson | |
| 6,206,822 B1 | 3/2001 | Foley | |
| 6,206,826 B1 | 3/2001 | Mathews et al. | |
| 6,206,885 B1 | 3/2001 | Ghahremani et al. | |
| 6,206,922 B1 | 3/2001 | Zdeblick et al. | 623/17.11 |
| 6,206,923 B1 | 3/2001 | Boyd et al. | 623/17.11 |
| 6,210,413 B1 | 4/2001 | Justis et al. | |
| 6,214,004 B1 | 4/2001 | Coker | |
| 6,217,509 B1 | 4/2001 | Foley | |
| 6,224,597 B1 | 5/2001 | Coker | |
| 6,224,608 B1 | 5/2001 | Ciccolella | |
| 6,224,631 B1 | 5/2001 | Kohrs | 623/17.11 |
| 6,231,575 B1 | 5/2001 | Krag | |
| 6,235,030 B1 | 5/2001 | Zucherman et al. | 606/61 |
| 6,238,397 B1 | 5/2001 | Zucherman et al. | 606/61 |
| 6,245,072 B1 | 6/2001 | Zdeblick et al. | 606/61 |
| 6,248,104 B1 | 6/2001 | Chopin et al. | |
| 6,248,106 B1 | 6/2001 | Ferree | 606/61 |
| 6,258,097 B1 | 7/2001 | Cook | |
| 6,261,287 B1 | 7/2001 | Metz-Stavenhagen | 606/61 |
| 6,264,658 B1 | 7/2001 | Lee et al. | 606/61 |
| 6,267,763 B1 | 7/2001 | Castro | 606/61 |
| 6,267,764 B1 | 7/2001 | Elberg | 606/61 |
| 6,267,765 B1 * | 7/2001 | Taylor et al. | 606/61 |
| 6,270,498 B1 | 8/2001 | Michelson | |
| 6,273,914 B1 | 8/2001 | Papas | |
| 6,283,966 B1 | 9/2001 | Houfburg | |
| 6,287,309 B1 | 9/2001 | Baccelli et al. | |
| 6,287,313 B1 | 9/2001 | Sasso | |
| 6,287,343 B1 | 9/2001 | Kuslich et al. | 623/17.11 |
| 6,290,700 B1 | 9/2001 | Schmotzer | 606/61 |
| 6,293,949 B1 | 9/2001 | Justis et al. | 606/61 |
| 6,296,609 B1 | 10/2001 | Brau | |
| 6,299,614 B1 | 10/2001 | Kretschmer et al. | |
| 6,302,842 B1 | 10/2001 | Auerbach et al. | |
| 6,309,390 B1 | 10/2001 | Le Couedic et al. | |
| 6,309,391 B1 | 10/2001 | Crandall et al. | |
| 6,312,432 B1 | 11/2001 | Leppelmeier | |
| 6,332,883 B1 | 12/2001 | Zucherman et al. | 606/61 |
| 6,875,211 B2 | 12/2001 | Nichols et al. | |
| 6,342,057 B1 | 1/2002 | Brace | |
| 6,348,058 B1 | 2/2002 | Melkent et al. | |
| 6,354,176 B1 | 3/2002 | Nordlin | |
| 6,355,038 B1 | 3/2002 | Pisharodi | |
| 6,361,541 B1 | 3/2002 | Barnhart | |
| 6,368,320 B1 | 4/2002 | Le Couedic et al. | |
| 6,368,350 B1 | 4/2002 | Erickson et al. | 623/17.14 |
| 6,368,351 B1 | 4/2002 | Glenn et al. | 623/17.15 |
| 6,371,959 B1 | 4/2002 | Trice | |
| 6,371,968 B1 | 4/2002 | Kogasaka | |
| 6,391,058 B1 | 5/2002 | Kuslich et al. | 623/17.11 |
| 6,395,033 B1 | 5/2002 | Pepper | 623/17.13 |
| 6,418,821 B1 | 7/2002 | Yamakawa | |
| 6,425,901 B1 | 7/2002 | Zhu et al. | |
| 6,428,472 B1 | 8/2002 | Haas | |
| 6,440,169 B1 | 8/2002 | Elberg et al. | 623/17.16 |
| 6,440,170 B1 | 8/2002 | Jackson | |
| 6,443,953 B1 | 9/2002 | Perra et al. | |
| 6,443,989 B1 | 9/2002 | Jackson | 623/17.15 |
| 6,461,330 B1 | 10/2002 | Miyagi | |
| 6,461,359 B1 | 10/2002 | Tribus et al. | |
| 6,471,724 B2 | 10/2002 | Zdeblick | |
| 6,478,798 B1 | 11/2002 | Howland | |
| D466,766 S | 12/2002 | Marty | |
| 6,506,151 B2 | 1/2003 | Estes | |
| 6,520,907 B1 | 2/2003 | Foley | |
| 6,524,238 B2 | 2/2003 | Velikaris et al. | |
| 6,530,880 B2 | 3/2003 | Pagliuca | |
| 6,530,926 B1 | 3/2003 | Davison | |
| 6,540,756 B1 | 4/2003 | Vaughan | |
| 6,551,320 B2 | 4/2003 | Lieberman | 606/61 |
| 6,554,831 B1 * | 4/2003 | Rivard et al. | 606/61 |
| 6,554,834 B1 * | 4/2003 | Crozet et al. | 606/65 |
| 6,562,046 B2 | 5/2003 | Sasso | |
| 6,562,073 B2 | 5/2003 | Foley | |
| 6,565,569 B1 | 5/2003 | Assaker et al. | 606/61 |
| 6,569,164 B1 | 5/2003 | Assaker et al. | |
| 6,576,017 B2 | 6/2003 | Foley et al. | |
| 6,579,292 B2 | 6/2003 | Taylor | |
| 6,585,738 B1 | 7/2003 | Mangione et al. | |
| 6,585,769 B1 | 7/2003 | Muhanna et al. | |
| 6,595,993 B2 | 7/2003 | Donno et al. | |
| 6,610,062 B2 | 8/2003 | Bailey et al. | |
| 6,626,904 B1 | 9/2003 | Jammet et al. | |
| 6,626,906 B1 | 9/2003 | Young | |
| 6,648,887 B2 | 11/2003 | Ashman | |
| 6,671,725 B1 | 12/2003 | Noel, Jr. et al. | |
| 6,676,661 B1 | 1/2004 | Benlloch et al. | |
| 6,679,833 B2 | 1/2004 | Smith et al. | |
| 6,682,532 B2 | 1/2004 | Johnson et al. | |

| | | |
|---|---|---|
| 6,685,705 B1 | 2/2004 | Taylor |
| 6,692,434 B2 | 2/2004 | Ritland |
| 6,736,816 B2 * | 5/2004 | Ritland .......... 606/61 |
| 6,743,257 B2 | 6/2004 | Castro |
| 6,749,613 B1 | 6/2004 | Conchy et al. |
| 6,749,614 B2 | 6/2004 | Teitelbaum et al. |
| 6,752,832 B2 | 6/2004 | Neumann |
| 6,761,719 B2 | 7/2004 | Justis et al. |
| 6,783,528 B2 | 8/2004 | Vincent-Prestigiacomo |
| 6,851,430 B2 | 2/2005 | Tsou |
| 6,916,319 B2 | 7/2005 | Munting |
| 6,916,330 B2 | 7/2005 | Simonson |
| 6,929,606 B2 | 8/2005 | Ritland |
| 6,951,538 B2 | 10/2005 | Ritland |
| 6,955,678 B2 | 10/2005 | Gabriel et al. |
| 6,966,910 B2 | 11/2005 | Ritland |
| 6,974,480 B2 | 12/2005 | Messerli et al. |
| 6,991,632 B2 | 1/2006 | Ritland |
| 7,008,431 B2 | 3/2006 | Simonson |
| 7,166,073 B2 | 1/2007 | Ritland |
| 7,207,992 B2 | 4/2007 | Ritland |
| 2001/0005796 A1 | 6/2001 | Zdeblick et al. .......... 623/17.11 |
| 2001/0010021 A1 | 7/2001 | Boyd et al. .............. 623/17.13 |
| 2001/0012942 A1 | 8/2001 | Estes |
| 2001/0027320 A1 | 10/2001 | Sasso |
| 2001/0047207 A1 | 11/2001 | Michelson ............... 623/17.11 |
| 2002/0011135 A1 | 1/2002 | Hall |
| 2002/0016592 A1 | 2/2002 | Branch |
| 2002/0022764 A1 | 2/2002 | Smith |
| 2002/0029082 A1 | 3/2002 | Muhanna ................. 623/17.11 |
| 2002/0049368 A1 | 4/2002 | Ritland |
| 2002/0058948 A1 | 5/2002 | Arlettaz |
| 2002/0068973 A1 | 6/2002 | Jackson ................... 623/17.11 |
| 2002/0068975 A1 | 6/2002 | Teitelbaum et al. ...... 623/17.11 |
| 2002/0077632 A1 | 6/2002 | Tsou |
| 2002/0082695 A1 | 6/2002 | Neumann |
| 2002/0107571 A1 | 8/2002 | Foley ....................... 623/17.11 |
| 2002/0107572 A1 | 8/2002 | Foley et al. .............. 623/17.11 |
| 2002/0120270 A1 | 8/2002 | Trieu et al. ..................... 606/61 |
| 2002/0123668 A1 | 9/2002 | Ritland |
| 2002/0143235 A1 | 10/2002 | Pagliuca |
| 2003/0083688 A1 | 5/2003 | Simonson |
| 2003/0083689 A1 | 5/2003 | Simonson |
| 2003/0093078 A1 | 5/2003 | Ritland ....................... 606/73 |
| 2003/0109880 A1 | 6/2003 | Shirado et al. |
| 2003/0139812 A1 | 7/2003 | Garcia et al. |
| 2003/0144665 A1 | 7/2003 | Munting ....................... 606/61 |
| 2003/0171749 A1 | 9/2003 | Le Couedic et al. ........... 606/61 |
| 2003/0171751 A1 | 9/2003 | Ritland ......................... 606/61 |
| 2003/0187431 A1 | 10/2003 | Simonson |
| 2003/0191470 A1 | 10/2003 | Ritland ......................... 606/61 |
| 2003/0220689 A1 | 11/2003 | Ritland |
| 2003/0236447 A1 | 12/2003 | Ritland |
| 2004/0002708 A1 | 1/2004 | Ritland ......................... 606/61 |
| 2004/0106997 A1 | 6/2004 | Lieberson |
| 2004/0138534 A1 | 7/2004 | Ritland |
| 2004/0181223 A1 | 9/2004 | Ritland |
| 2004/0254428 A1 | 12/2004 | Ritland |
| 2005/0004593 A1 | 1/2005 | Simonson |
| 2005/0020920 A1 | 1/2005 | Ritland |
| 2005/0027360 A1 | 2/2005 | Webb et al. |
| 2005/0119656 A1 | 6/2005 | Ferrante et al. |
| 2005/0143737 A1 | 6/2005 | Paffard et al. |
| 2005/0149023 A1 | 7/2005 | Ritland |
| 2005/0149191 A1 | 7/2005 | Cragg et al. |
| 2005/0203517 A1 | 9/2005 | Jahng et al. |
| 2005/0203519 A1 | 9/2005 | Harms et al. |
| 2005/0209694 A1 | 9/2005 | Loeb |
| 2005/0228233 A1 | 10/2005 | Ritland |
| 2006/0009768 A1 | 1/2006 | Ritland |
| 2006/0041259 A1 | 2/2006 | Paul et al. |
| 2006/0064090 A1 | 3/2006 | Park |
| 2006/0069390 A1 | 3/2006 | Frigg et al. |
| 2006/0079899 A1 | 4/2006 | Ritland |
| 2006/0195087 A1 | 8/2006 | Sacher et al. |
| 2007/0016193 A1 | 1/2007 | Ritland |

FOREIGN PATENT DOCUMENTS

| | | |
|---|---|---|
| EP | 0 820 731 A3 | 1/1998 |
| FR | 2796828 | 2/2001 |
| FR | 2812185 | 2/2002 |
| JP | 2000-33091 | 2/2000 |
| WO | 96/29947 | 10/1996 |
| WO | 97/06742 | 2/1997 |
| WO | WO 99/40866 | 8/1999 |
| WO | WO 00/18305 | 4/2000 |
| WO | 00/57801 | 5/2000 |
| WO | 01/67973 | 9/2001 |
| WO | WO 02/02022 | 1/2002 |
| WO | WO 02/07621 | 1/2002 |
| WO | 02/36026 | 5/2002 |
| WO | WO 02/060330 | 8/2002 |
| WO | WO 03/026523 | 4/2003 |
| WO | WO 03/073908 | 9/2003 |
| WO | WO 03/094699 | 11/2003 |
| WO | WO 2004/075778 | 9/2004 |
| WO | WO 2004/089244 | 10/2004 |

OTHER PUBLICATIONS

Caspar; "Technique of Microsurgery: Microsurgery of the Lumbar Spine: Principles and Techniques in Spine Surgery"; *Aspen Publications*; 1990; 105-122.

Hilton et al.; "Meditronic Sofamor Danek METRX Microdiscectomy Surgical Technique Brochure"; 2000.

Kambin; "Arthroscopic Microdiscectomy: Minimal Intervention in Spinal Surgery"; *National Library of Medicine*; 1991; 67-100.

Savitz; "Same-Day Microsurgical Arthroscopic Latera-Approach Laser-Assisted (Small) Fluoroscopic Discectomy"; *Journal of Neurosurgery*; Jun. 1994; 1039-1045.

Schaffer et al.; "Percutaneous Posterolateral Lumbar Discectomy and Decompression with a 6.9 Millimeter Cannula"; *Journal of Bone and Joint Surgery*; 1991; 822-831.

Wiltse; "New Uses and Refinements of the Paraspinal Approach to the Lumbar Spine"; *Spine*; 1988; 13(6):696-706.

China Chemical Reporter, "Rapid Development of Polyether Ether Ketone", CNCIC Chemdata Inc., 2004, 2 pages.

Green, "Body Building—Medical Materials for Systems and Scaffolding," Materials World, Journal of the Institute of Materials, vol. 10, No. 2, 2001, 4 pages.

Green, et al., "A Polyaryletherketone Biomaterial for Use in Medical Implant Applications," Lancashire, United Kingdom, 2001, 1 page.

U.S. Appl. No. 10/165,991, Simonson.

U.S. Appl. No. 11/425,987, Ritland.

Invibio, Biomaterials Solutions, "PEEK-Classix," Invibio Inc., Lancashire, United Kingdom, 2003, 2 pages.

Invibio, Biomaterials Solutions, "PEEK-Optima Polymer: Performance Purity Flexibility Endurance," Invibio Inc., Lancashire, United Kingdom, 2004, 3 pages.

Sofamor Danek Video Systems Brochure.

Tangram Technology Ltd., "Polymer Data File: Polyether Ether Keotone-PEEK," Available at http://www.tangram.co.uk/TI-Polymer-PEEK.html, 2001, 5 pages.

Web pages, http://www.brainlab.com, Apr. 2, 2002; 5 pp.

International Search Report for PCT Application Serial No. PCT/US01/21205 mailed Sep. 13, 2001.

Written Opinion for PCT Application Serial No. PCT/US01/21205 mailed Jun. 10, 2002.

International Preliminary Examination Report for PCT Application Serial No. PCT/US01/21205 mailed Apr. 23, 2003.

Office Action dated Dec. 1, 2008, issued in related and co-pending Canadian Application No. 2,415,072.

Office Action dated Aug. 21, 2008, related Australian Application No. 2006200772.

Office Action dated Aug. 21, 2008, issued in Australian Application No. 2006200772.

International Search Report dated Sep. 13, 2001, issued in Application PCT/US2001/021205.
Written Opinion dated Jun. 10, 2002, issued in Application PCT/US2001/021205.
International Preliminary Examination Report dated Mar. 4, 2003, issued in Application PCT/US2001/021205.
Notice of Allowance and Approved Claim Set dated Mar. 20, 2009, issued in Australian Application No. 200600772.
Search Report, dated Nov. 19, 2009, issued in EPO Application No. 01958866.4.
Office Action dated Jan. 22, 2009, issued in U.S. Appl. No. 11/283,006.
Final Office Action dated Oct. 28, 2009, issued in U.S. Appl. No. 11/283,006.
Office Action dated Mar. 28, 2006, issued in U.S. Appl. No. 10/262,574.
Office Action dated Nov. 21, 2008, issued in Australian Application No. 2004216131.
Notice of Allowance dated Nov. 27, 2009, issued in Australian Application No. 2004216131.
Office Action dated May 13, 2008, issued in U.S. Appl. No. 11/069,390.
Final Office Action dated Dec. 24, 2008, issued in U.S. Appl. No. 11/069,390.
Office Action dated May 18, 2009, issued in U.S. Appl. No. 11/069,390.
Notice of Allowance dated Nov. 9, 2009, issued in U.S. Appl. No. 11/069,390.
Office Action dated Feb. 23, 2009, issued in U.S. Appl. No. 11/669,015.
Final Office Action dated Nov. 23, 2009, issued in U.S. Appl. No. 11/669,015.
International Search Report dated Feb. 19, 2003, issued in Application No. PCT/US02/31201.
Written Opinion dated Aug. 14, 2003, issued in Application No. PCT/US02/31201.
International Preliminary Examination Report dated Dec. 5, 2003, issued in Application No. PCT/US02/31201.
International Search Report dated Mar. 3, 2005, issued in Application No. PCT/US04/05751.
Written Opinion dated Mar. 3, 2005, issued in Application No. PCT/US04/05751.
International Preliminary Examination Report dated Aug. 26, 2005, issued in Application No. PCT/US04/05751.
Supplemental Search Report dated Jul. 29, 2009, issued in European Application No. 02763815.4.
Office Action dated Oct. 21, 2009, issued in Japanese Application No. 2006-503886.
Office Action dated Nov. 4, 2009, issued in Canadian Application No. 2415072.
Office Action dated Oct. 12, 2009, issued in European Application No. 02763815.4.

* cited by examiner

POLYAXIAL CONNECTION DEVICE AND METHOD

CROSS REFERENCE TO RELATED APPLICATIONS

This application is a divisional of U.S. patent application Ser. No. 09/898,478 filed on Jul. 2, 2001 now U.S. Pat. No. 6,736,816 and entitled "POLYAXIAL CONNECTION DEVICE AND METHOD", which claimed priority from U.S. Provisional Patent Application No. 60/215,602 filed on Jun. 30, 2000. The entire disclosures of these applications are considered to be part of the disclosure of the present application and are hereby incorporated by reference in their entirety.

FIELD OF THE INVENTION

This invention relates generally to polyaxial securement devices and, more particularly, to a screw for insertion into human bone having a polyaxial coupling for adjustably mounting a foreign object to the bone and, even more particularly, to a screw for insertion into spinal bone having a polyaxial coupling and locking mechanism for mounting a stabilizing rod to a sequence of vertebrae.

BACKGROUND OF THE INVENTION

The use of fixation devices for the treatment of vertebrae deformities and injuries is well known in the art. Various fixation devices are used in medical treatment to correct curvatures and deformities, treat trauma and remedy various abnormal spinal conditions. Treatment of these conditions generally requires the implantation of various component pieces such as support rods, crosslinks, caudal facing hooks, cranial facing hooks and like components, which form a spinal implant system.

It is necessary in spinal implant systems to properly anchor the system to bone to provide necessary support of the implant. Bone screws are commonly used for anchoring spinal implant systems. However, there are several problems with the use of fixed screws for anchoring spinal implants. The exact final position of a bone screw is difficult, if not impossible, to predict prior to the exposure of the patient's bone. This unpredictability results from the uncertainty of exact bone formation and shape within an individual patient. Additionally, it can be difficult to predetermine the structure of the bone, i.e. whether the bone is soft or even osteoporotic. Even if the final position of the screw can be predetermined, the necessary shape and position of a spinal rod implant may create unwanted stress upon the bone screw or the bone itself. This is especially true where a plurality of screws is required along the spinal column for securement of an implant. The alignment of the rod with several screws along the vertebrae compounds this problem and makes undesired stress much more probable. Moreover, this misalignment may influence the extent and speed of correction of the spinal defect.

It is thus desirable to have a polyaxial securement method. There exists a number of patents drawn to polyaxial bone screws. Unfortunately, the advantage of many of these designs comes at the expense of bulk in the connection means or complexity of implantation. As the size of a bone screw increases, so too does the displacement of normal bodily formations, such as muscular tissue or bone. It is common in the insertion of spinal implants to necessarily remove portions of vertebral bone to allow proper insertion of a bone screw. Moreover, this bulk may result in long-term muscular displacement that may lead to a patient's pain or discomfort. Increased complexity of the installation procedure is undesirable because it increases a patient's time in surgery. Increased operating time is known to increase the risk of many complications associated with surgery. The additional time necessary to remove, or even temporarily dislocate, bone or muscular tissue also increases operating time, and thus the risk of complications.

It is also desirable with some patients to have a spinal implant system that allows the vertebral column to settle naturally under the weight of the human body. Human bone heals more readily under some pressure. In a rigid spinal implant system, the patient's spinal column may be unnaturally held apart by the structure of the implant. It is possible that this stretching of the vertebrae, in relation to one another, results in delayed or incomplete healing of the bone.

In view of the above, there is a long felt but unsolved need for a method and system that avoids the above-mentioned deficiencies of the prior art and that provides an effective system that is relatively simple to employ and requires minimal displacement or removal of bodily tissue.

SUMMARY OF THE INVENTION

In accordance with the present invention, a polyaxial connector device is provided with a socket for receiving a headed connecting link. A surgical implant assembly employing the polyaxial connector device is also disclosed. The surgical implant assembly of the present invention includes an attachment device, a headed anchor shaft (or tension link), and a connector. The attachment device of the present invention has a shank with a securement mechanism on one end and an enlarged area on the other end. The securement mechanism may be selected from any known method of securing one article to another, for example, a hook, a plate, a flanged device, or an adhesive, however, it is anticipated that the most common securement mechanism used will be screw threads. The enlarged area includes a hollow core, i.e., a socket, and a central aperture providing access to the hollow core. The enlarged area need only be large enough to envelop the head of the anchoring shaft and provide a wall thickness necessary for strength considerations.

The attachment device may include additional features to enable the insertion of the head end of the tension link into the hollow core. The enlarged area of the attachment device may include an entry channel, leading to the hollow core, that accommodates the tension link head end so that the tension link may be advanced, shaft end first, until the head of the tension link is positioned within the hollow core. Additionally, the entry channel and the central aperture may be connected by an slot through the wall of the enlarged area. In this way, the tension link head end may be positioned within the hollow core without extending the entire length of the tension link beyond the enlarged area of the attachment device opposite the central aperture. The surgeon may place only the head end of the tension link at the entry channel, slide the tension link shaft through the tension link slot, and draw the head end into the hollow core. Alternatively, in lieu of an entry channel or tension link slot, the enlarged area may include one or more expansion slots. In this embodiment, the head of the tension link may be inserted into the hollow core through the central aperture by the application of enough force to expand the central aperture. Once the head of the tension link is properly received into the hollow core, the enlarged area returns to its original size and shape. Unwanted expansion of the enlarged area is prevented by the connector once the enlarged area is properly seated into a head receptacle on the connector during implantation. This maintains the head of the tension link within the hollow core.

The external surface of the enlarged area of the attachment device may be formed into one of limitless geometries. For example, the external surface may be spherical, or at least semi-spherical. The external surface may be at least slightly aspheric. By controlling the degree of asphericity, the contact surface between the attachment device and the connector can thereby control the degree of freedom of the connector relative to the attachment device. Alternatively, the external surface may be conical, or a truncated cone shape, to allow rotational freedom while maintaining a coaxial relationship between the attachment device and the connector. Also, the external surface may be polyhedral or provided with facets to allow angular displacement in only finite steps or prevented altogether. In embodiments including conical, truncated cone shape, polyhedral or faceted geometries of the external surface of the enlarged area, the mating head receptacle of the connector may have corresponding geometry.

The tension link secures and maintains the position of the connector relative to the attachment device. The tension link is a shaft with a head end and a thread end. The head end, as described above, is contained within the hollow core of the attachment device. The threaded end extends through the connector and is secured to the connector by a link nut threaded onto the thread end.

The tension link may be provided with a projection to prevent undesirable rotation of the link when tightening or loosening the link nut, yet still enable angular displacement necessary to provide a polyaxial connection. In one embodiment, a link retainer, or a projection, may be provided on the shaft of the tension link. In this embodiment, it is necessary to provide a link retainer recess within the tension link cavity of the connector. In an alternative embodiment, the link retainer, or projection, may be provided at the intersection of the tension link shaft and the head end, and extending over a portion of the surface of the head end. In this embodiment, used with the attachment device embodiment including a tension link slot, the rotation may be prevented by contacting the link retainer with one side of the tension link slot. In either of the two foregoing embodiments, it is desirable to undersize the link retainer, relative to the link retainer recess or the tension link slot, so that the polyaxial freedom of the tension link and attachment device combination is not unduly limited. In an alternative embodiment, a retaining process, or small projection, may be provided on the tension link head. The retaining process should be positioned such that the retaining process is within the entry channel. Undesired rotation may be prevented by contacting the small projection with the wall of the entry channel.

The connector couples the attachment device to the implant component, such as a spinal rod implant. The connector has a connecting end with a head receptacle, a rod end with a rod aperture, and a tension link cavity. The tension link, with its head positioned in the hollow core of the attachment device, is inserted through the tension link cavity so that an enlarged area of the attachment device nests in the head receptacle. The rod aperture secures the implant component in a desired position. The rod aperture may be secured by the tension link when the link nut is threaded and tightened on the link. In this embodiment, the rod end of the connector has a gap on one side of the rod aperture. The tension link cavity extends continuously through the tension link on both sides of the gap. The upper portion of the rod end forms a tab. As the tab is drawn toward the receiver end of the connector the gap narrows until the rod aperture firmly clamps the implant component or until the gap is drawn completely together.

In still other embodiments, it may also be desirable to provide a separate system for securing the connector to the attachment device and for securing the implant component to the connector. Therefore, in an alternative embodiment, the gap is connected to the rod aperture in a position that does not intersect the rod aperture. In this embodiment, a separate screw, or other connection device, is required to secure the implant component in the rod aperture. The tension link is then used to secure the connector to the attachment device.

In either of the two foregoing connector embodiments, it may be desirable to secure the rod within the rod aperture without clamping to the extent axial movement of the rod within the rod aperture is prevented. In this way, for example, the spine may settle under its own weight and provide a better healing environment for the bone. In conjunction with this embodiment, the implant component may be supplied with flanges, or other extensions to constrain axial movement of the implant component within a desired range.

To surgically implant a device of the present invention, the surgeon may attach an attachment device, selected from one of the embodiments of the present invention. After successful attachment, the surgeon may insert a tension link of the present invention by positioning the head end of the tension link within the hollow core of the attachment device. The surgeon may then place a connector, with a head receptacle designed for mating with the second end of the attachment device, upon the attachment device by inserting the tension link through the tension link cavity of the connector. At this point, the surgeon may select the desired angle of position of the connector for attaching a implant component. Once the connector is properly adjusted, the link nut may be secured to the tension link, thereby securing the elements together in the desired position. The link nut may be loosened, as necessary, to readjust the placement of the implant component. Alternatively, if a connector having a separate implant component securement device is used, the step of securing the link nut may be delayed until after the implant component is secured in the rod aperture and properly positioned.

Based on the foregoing summary, a number of worthwhile aspects of the present invention can be readily identified. A connector device is provided with a small and simple polyaxial adjustment mechanism. The minimal size of the enlarged area of the connector device allows attachment of the device to human bone without significant displacement of human tissue. Therefore, the complexity of surgery and the following pain and discomfort of the patient may be minimized. The polyaxial nature of the device, combined with the small size, may allow a surgeon to attach the securement device to a secure portion of the human body without the need to remove bony processes to accommodate a larger attachment device. Additionally, a simple surgical implant assembly, including the polyaxial attachment device, is provided. The simplicity of the elements, and the assembly process thereof, may reduce the patient's time in surgery, thus reducing the risk and probability of surgical complications. Finally, a number of embodiments of the present invention may be used in combination to allow the surgeon great latitude in selection of materials. The surgeon may select from different embodiments of the attachment device, the tension link, and the connector to best fit the surgical implant parameters. With these choices the surgeon may then best determine which embodiments of which elements to select to minimize removal or displacement of bodily tissue or bone, and thereby reduce both the patient's risk of surgical complications and post-surgical pain and discomfort.

Additional advantages of the present invention will become readily apparent from the following discussion, particularly when taken together with the accompanying drawings.

BRIEF DESCRIPTION OF THE DRAWINGS

FIG. 9b is a side elevation view of the tension link with link retainer shown in FIG. 7a;

FIG. 9c is an end view of the tension link with link retainer shown in FIG. 7a;

FIG. 10b is a side elevation view of the tension link with link retainer shown in FIG. 8a;

FIG. 19b is a plan view of the surgical implant assembly shown in FIG. 19a.

DETAILED DESCRIPTION OF THE PREFERRED EMBODIMENT

Figure 1A:
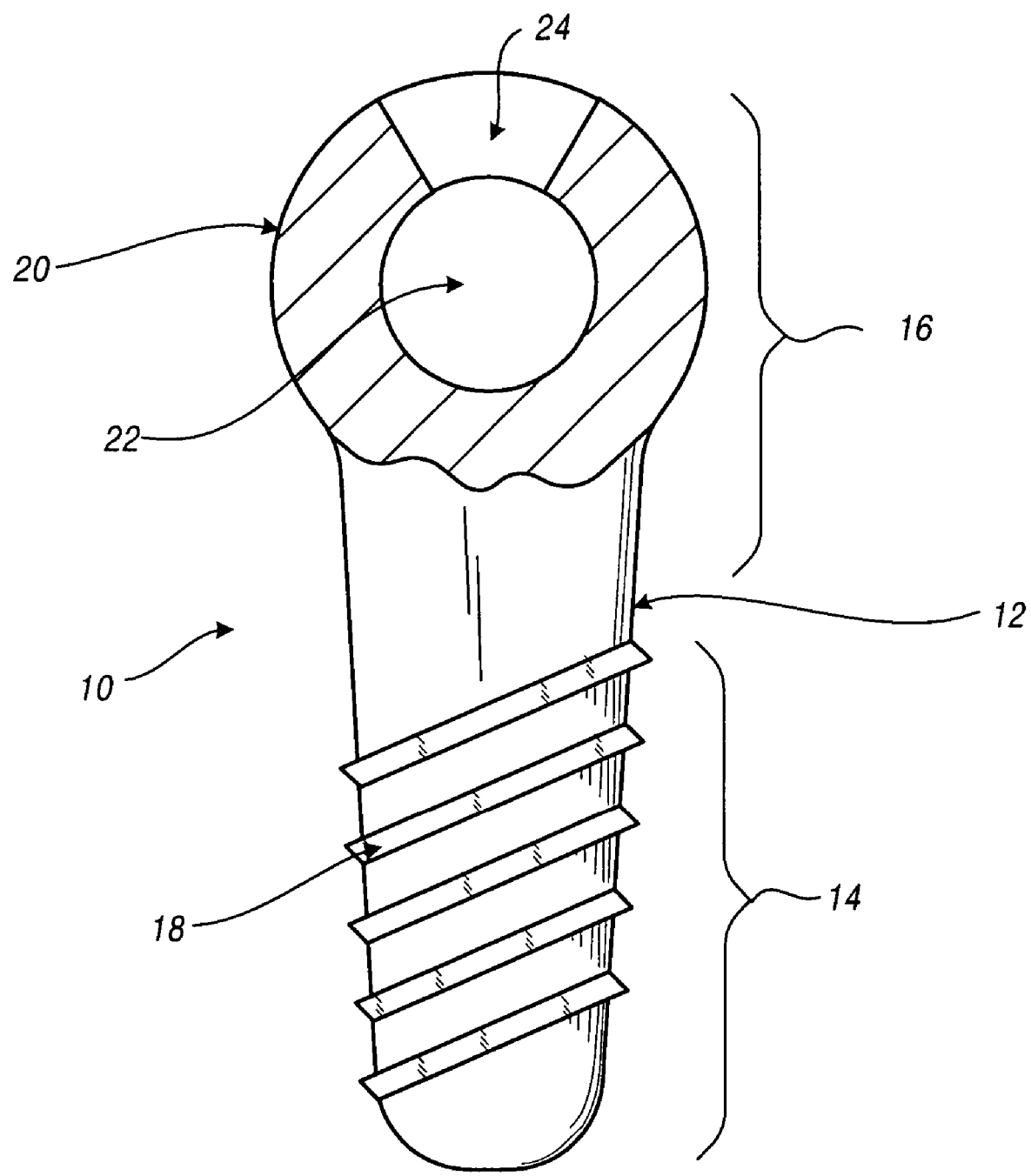
FIG. 1a is a partial cross-sectional view of one embodiment of the connector device of the present invention.
Figure 1B:
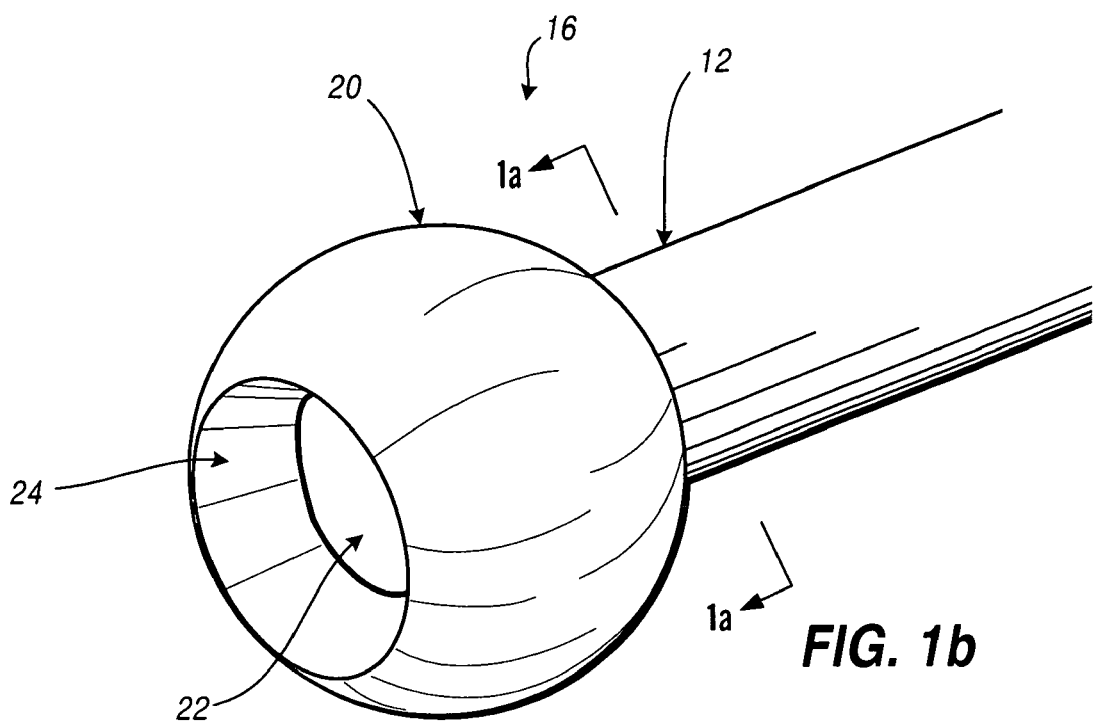
FIG. 1b is an end perspective view of an alternative embodiment of the connector device of the present invention.

With reference to FIG. 1, one embodiment of the attachment device (or connection device) of the present invention is shown in partial cross-section. The attachment device 10 includes a shank 12 having a first end 14 and a second end 16. The first end 14 of the shank 12 includes a securement mechanism 18. As shown in FIG. 1, the securement mechanism 18 may be screw threads. It is noted, however, that the securement mechanism 18 may include any known method of securing one item to another. For example, the securement mechanism 18 may be a hook, a plate, a flange, or adhesive. In the case of the securement mechanism 18 as a flange or plate, the securement mechanism 18 may require additional hardware such as screws, bolts, or adhesive to secure the plate or flange to the intended object. In the case of the securement mechanism 18 as an adhesive, or requiring the additional use of adhesive, the adhesive would necessarily be applied to the securement mechanism 18, not included within it. Additionally, adhesive could be used with the securement mechanism 18, e.g., applied to screw threads, for additional securement capacity.

The second end 16 of the shank 12 generally comprises an enlarged area 20 including a central core 22 and an aperture 24. The second end 16 of FIG. 1 is shown in cross-sectional view to more clearly show the central core 22 and the aperture 24.

Figure 2:
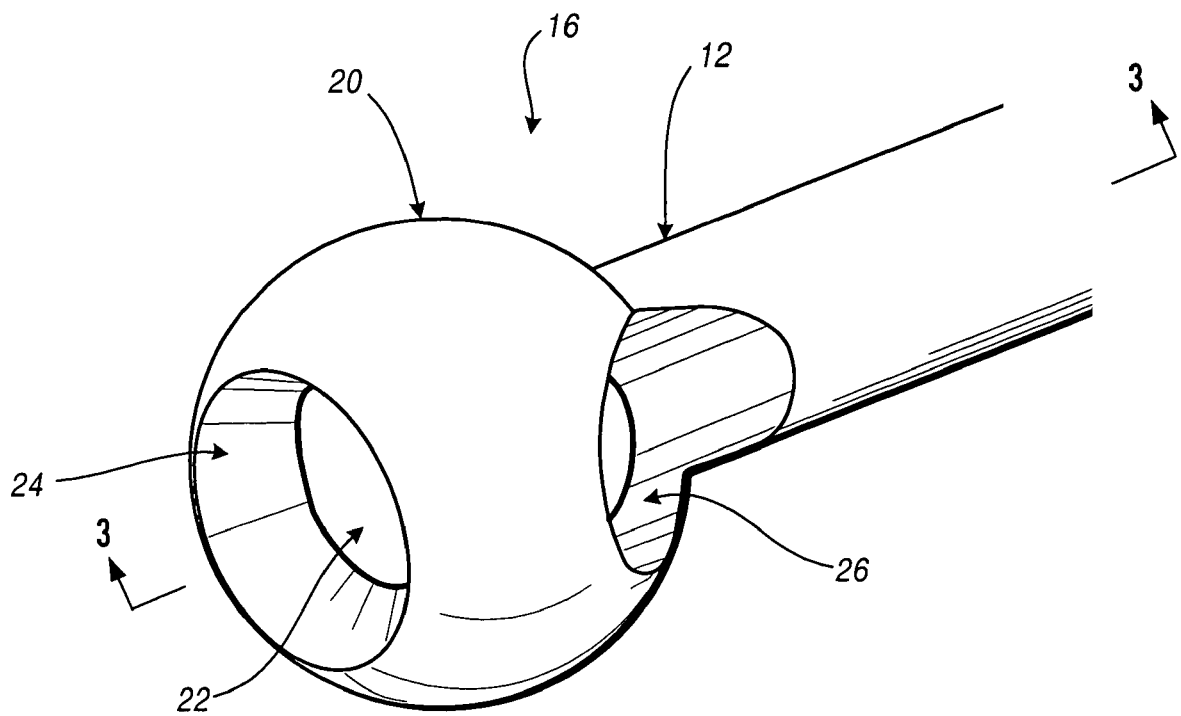
FIG. 2 is an end perspective view of an alternative embodiment of the connector device of the present invention.

With reference to FIG. 2, an embodiment of the second end 16 of the shank 12 is shown. In this embodiment, the enlarged area 20 includes a hollow core 22 and a central aperture 24. The enlarged area also includes an entry channel 26. The entry channel 26 is operatively connected with the hollow core 22 such that a tension link 28, having a shaft 30 with a threaded end 32 and a head end 34, may be inserted, threaded end 32 first, through the entry channel 26, the hollow core 22, and central aperture 24 until the head end 34 of the tension link 28 is retained within the hollow core 22 by the central aperture 24.

Figure 3:
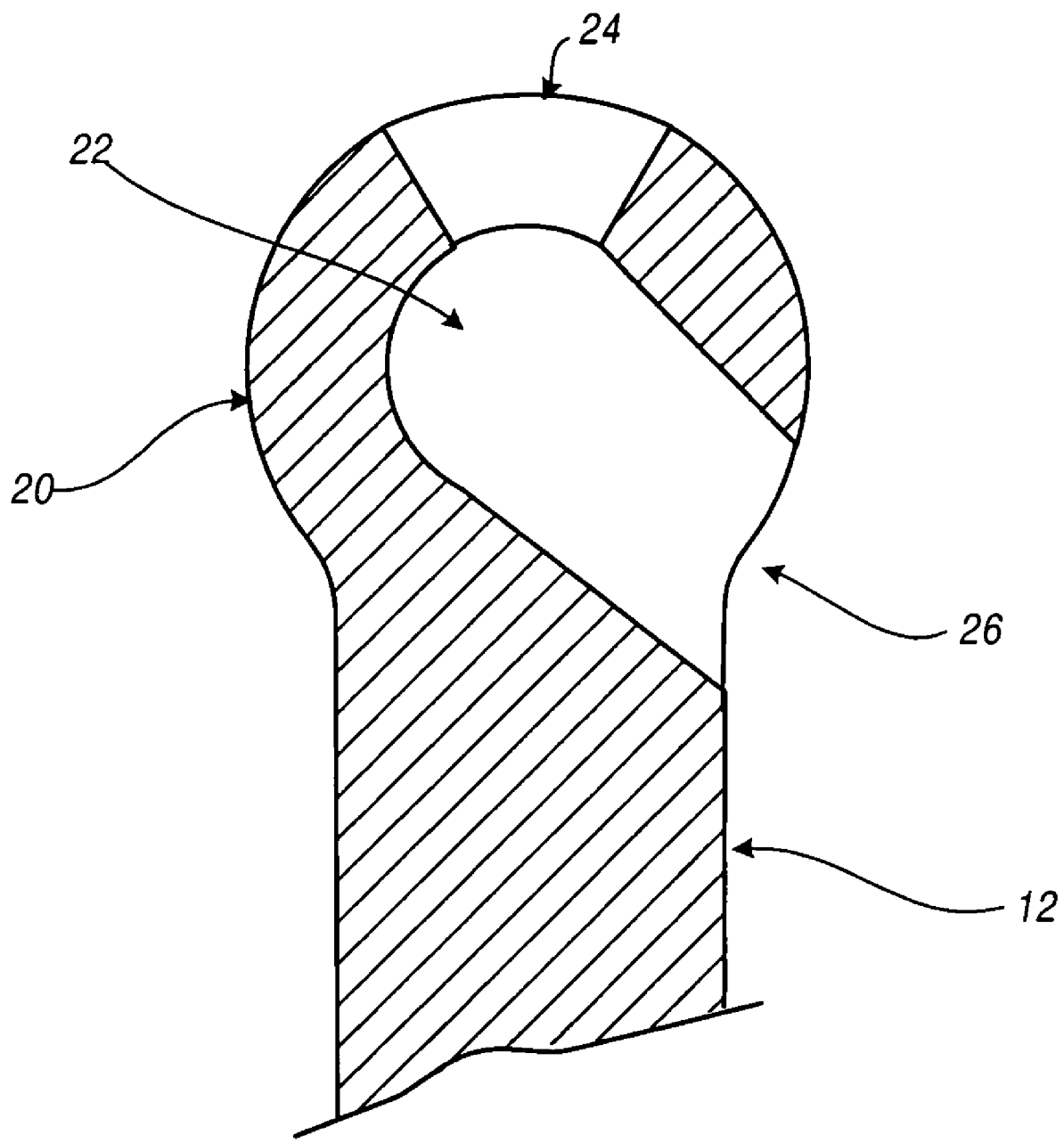
FIG. 3 is a cross-sectional view of the connector device shown if FIG. 2.

With reference to FIG. 3, the embodiment of the second end 16 of attachment device 10 is shown in cross-section. FIG. 3 clarifies the operational relationship between the entry channel 26, the hollow core 22 and the central aperture 24.

Figure 4:
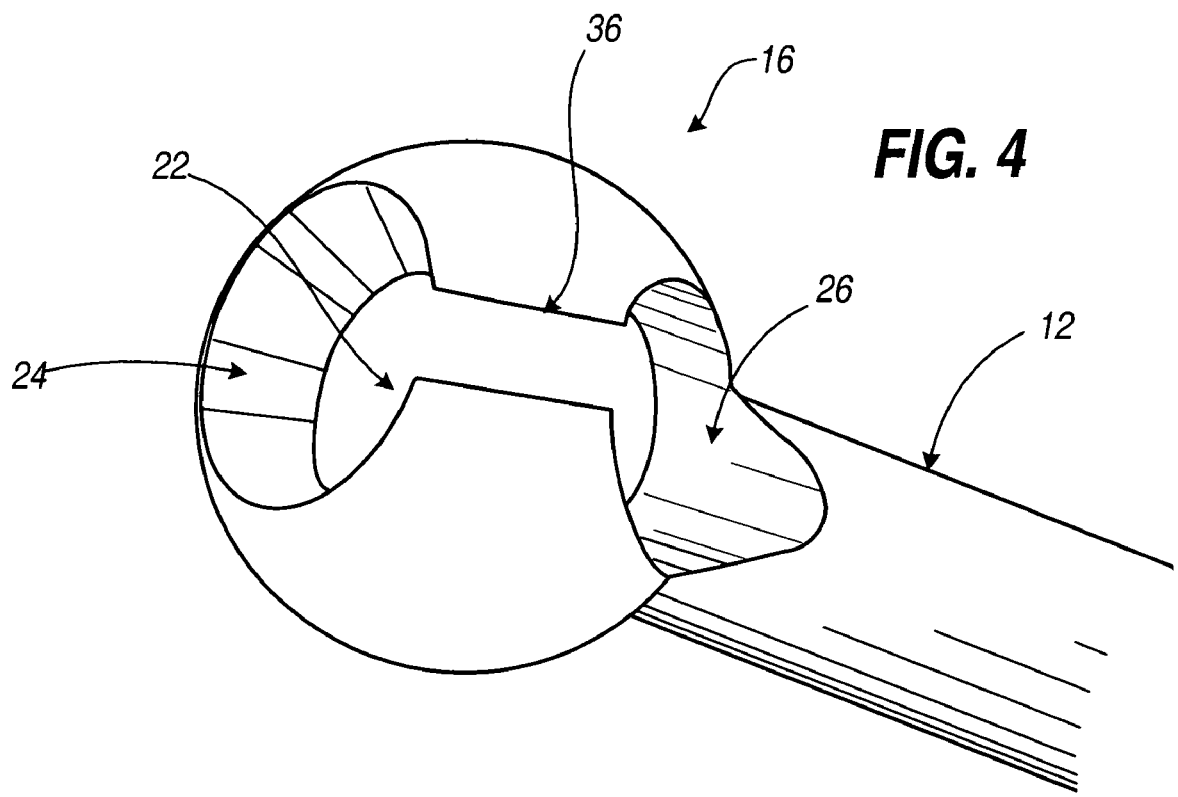
FIG. 4 is an end perspective view of another alternative embodiment of the connector device of the present invention.

With reference to FIG. 4, an alternative embodiment of the attachment device 10 is shown. This embodiment is similar to the embodiment of FIGS. 2 and 3, but with an additional element. In this embodiment, a tension link slot 36 is provided between the entry channel 26 and the central aperture 24. The tension link slot 36 allows the shaft 30 of the tension link 28 to be inserted through the tension link slot 36. In this way, the tension link 28 may be inserted through the tension link slot 36 to pass through both central aperture 24 and the entry channel 26. The tension link 28 may then be drawn through the aperture 24 until the tension link head end 34 passes through the entry channel 26 and rests in the hollow core 22. This embodiment may allow the surgeon to insert a tension link 28 into an attachment device 10 secured to the human body in cases where the obstacles, including the human body itself, or parts thereof, prevent the length of the tension link 28 from extending completely beyond the entry channel 26 opposite the central aperture 24.

Figure 5:
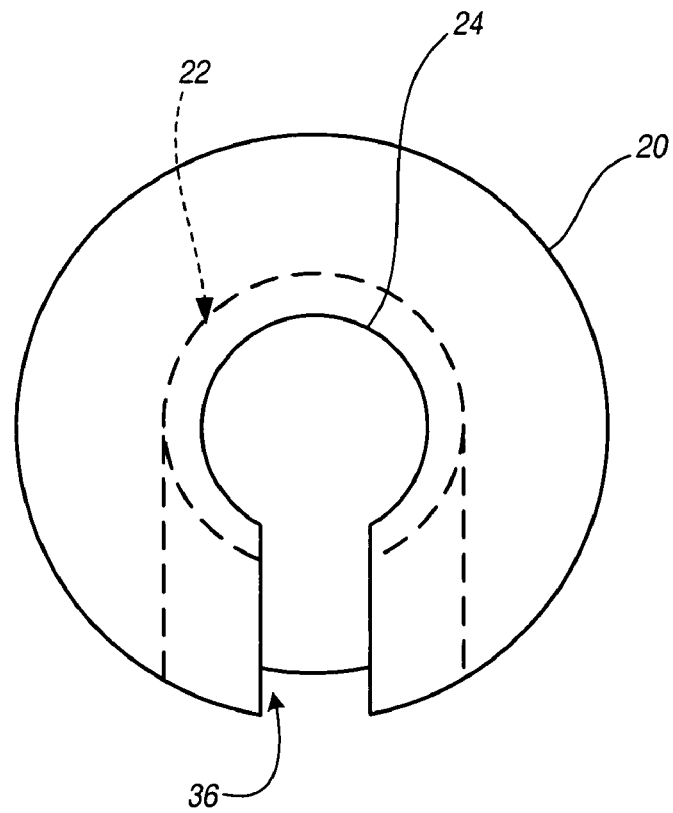
FIG. 5 is a top plan view of the connector device shown in FIG. 4.

FIG. 5 shows an end view, from the second end 16, of the embodiment of the attachment device 10 from FIG. 4. FIG. 5 clarifies the relationship between the tension link slot 36 and the central aperture 24, the hollow core 22 and the entry channel 26. It should be noted that the central aperture 24 is shown in FIG. 5 as located at top dead center of the enlarged portion 20 of the attachment device 10. However, the location of the central aperture 24 may be at any angular relationship to the shank 12. This location of the central aperture 24 applies to this, and every other, embodiment of the attachment device 10. The hollow core 22 should be sized to receive the head end 34 of the tension link 28, in this and other embodiments of the present invention. Similarly, the central aperture 24 should be sized to accommodate the tension link shaft 30, and with enough clearance to provide the desired angular displacement. For example, it may be desirable to provide from about 0 to 60 degrees of angular displacement of the tension link 28 from the longitudinal axis of the attachment device 10. In some instances, a smaller range may be advantageous.

Figure 6:
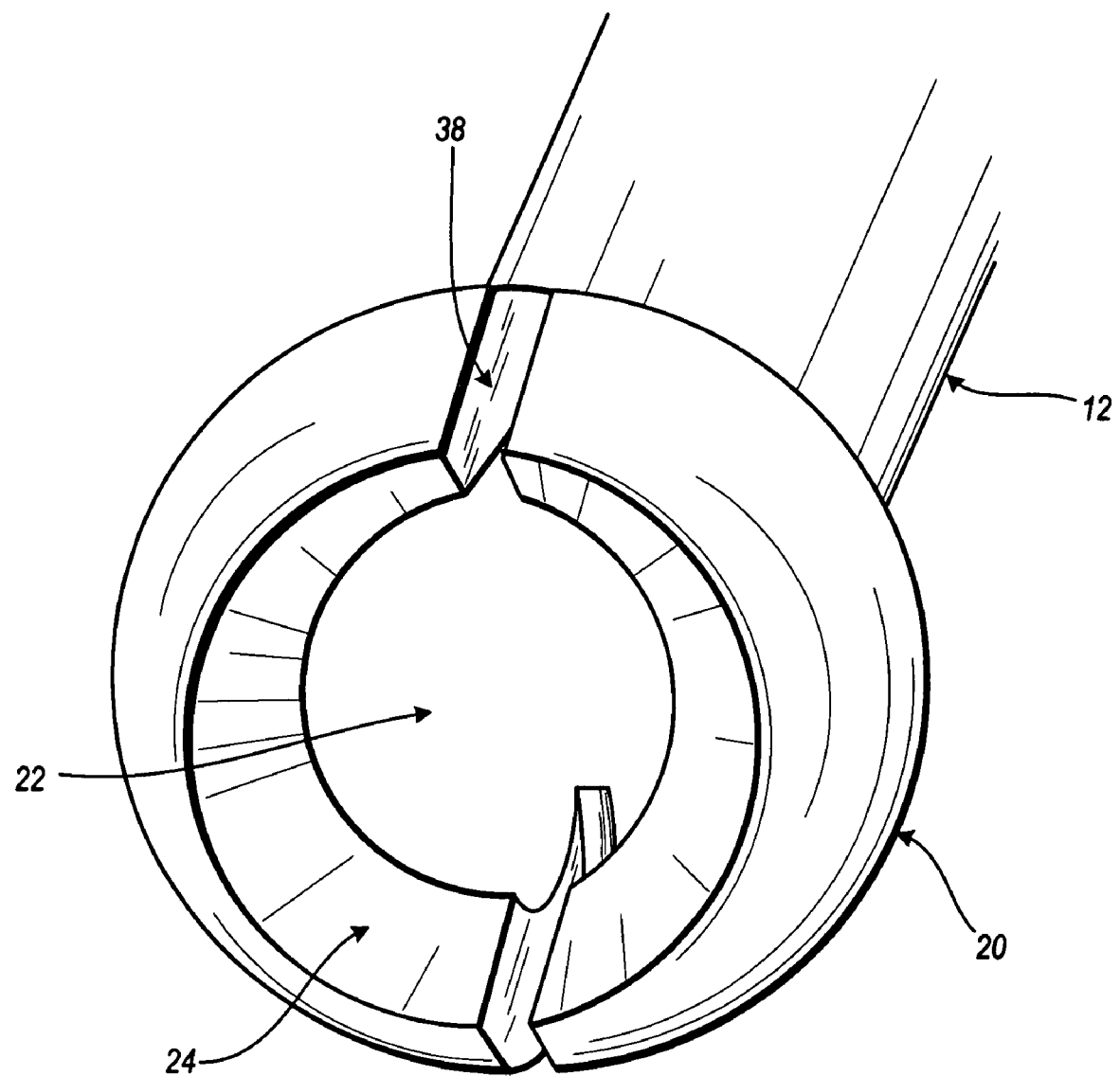
FIG. 6 is an end perspective view of yet another alternative embodiment of the connector device of the present invention.

With reference to FIG. 6, an additional alternative embodiment of the enlarged area 20 of the attachment device 10 is shown. In this embodiment, the enlarged area 20 includes a hollow core 22 and a central aperture 24, but does not include an entry channel 26. Instead, at least one expansion slot 38 extends from the central aperture 24 along the exterior surface of the enlarged area 20. The expansion slot 38 extends completely through the wall defined by the hollow core 22 and the exterior surface of the enlarged area 20. The embodiment of FIG. 6 includes two expansion slots 38 diametrically opposite from one another, however, the number of expansion slots 38 and their location in radial relation to the central aperture 24 may be selected in the design of the attachment device 10 according to, among other things, the application, or the size and material of construction of the attachment device 10. The expansion slots 38 may allow insertion of the head end 34 of the tension link 28 into the hollow core 22 through the central aperture 24 by allowing deformation of the enlarged area 20. As explained in more detail below, the connector 40, more specifically, the head receptacle 42 of the connector 40, when properly installed over the enlarged area 20 prevents further deformation of the enlarged area 20, and thus the central aperture 24 retains the head 34 of the tension link 28 within the hollow core 22.

Figure 7:
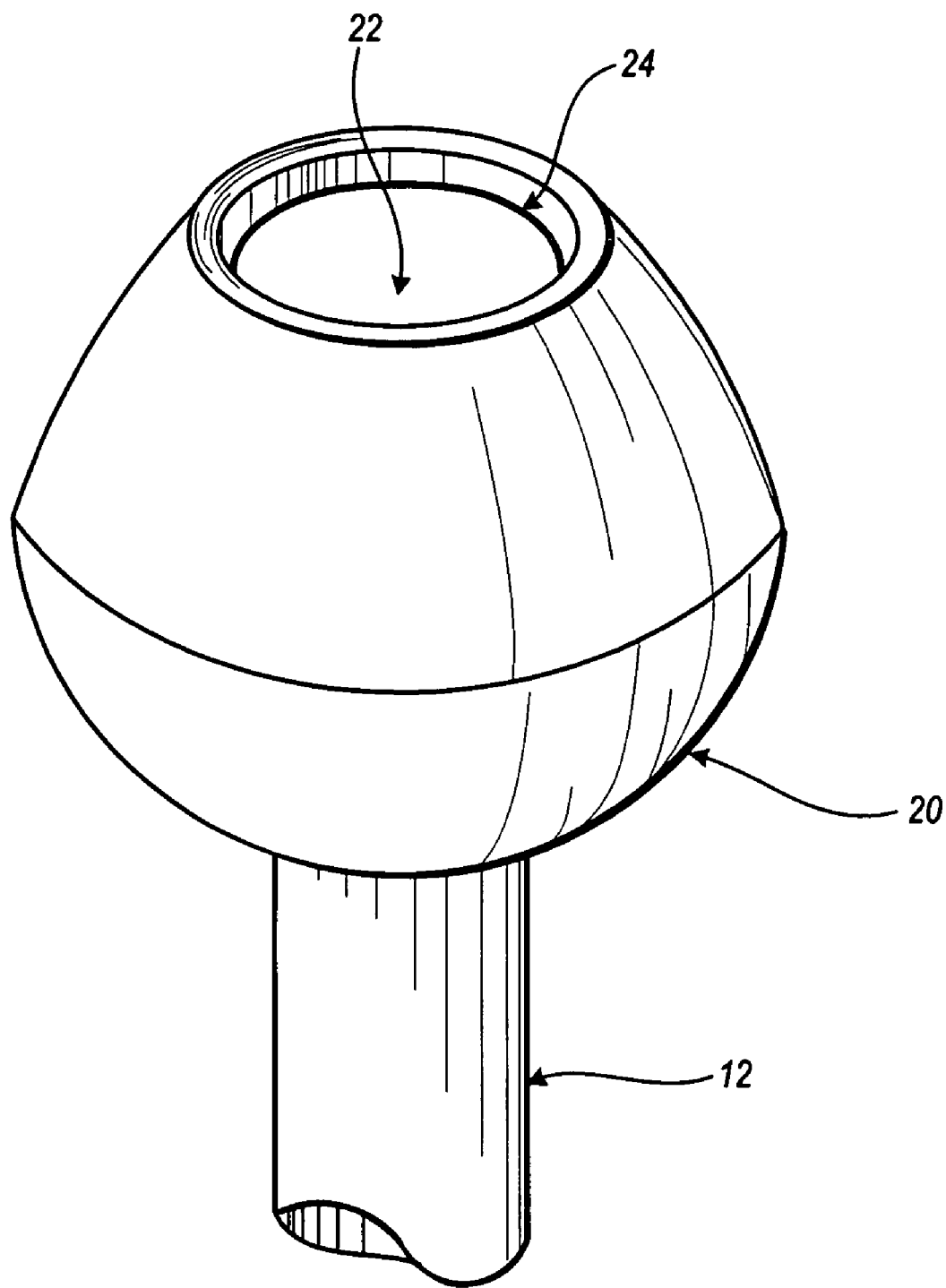
FIG. 7 is an end perspective view of still another alternative embodiment of the connector device of the present invention.

With reference to FIG. 7, yet another alternative embodiment of the enlarged area 20 of the attachment device 10 is shown. In this embodiment, at least a portion of the enlarged area 20 includes a substantially conical portion around the central aperture 24. The head receptacle 42 of the connector 40 has mating geometry to the enlarged area 20. Thus, the partially conical shape of the enlarged area 20 allows polyaxial positioning of the connector 40 while controlling movement in one degree of freedom. The connector 40 may rotate around the central axis of the conical section, however, the mating geometry of the head receptacle 42 prevents angular displacement relative to the central axis of the conical section. Obviously, the central aperture 24 may require that the shape of the enlarged area 20 not be truly conical. The central aperture 24 may necessitate the geometry of the enlarged area 20 to be more aptly described as a truncated cone shape.

Figure 8:
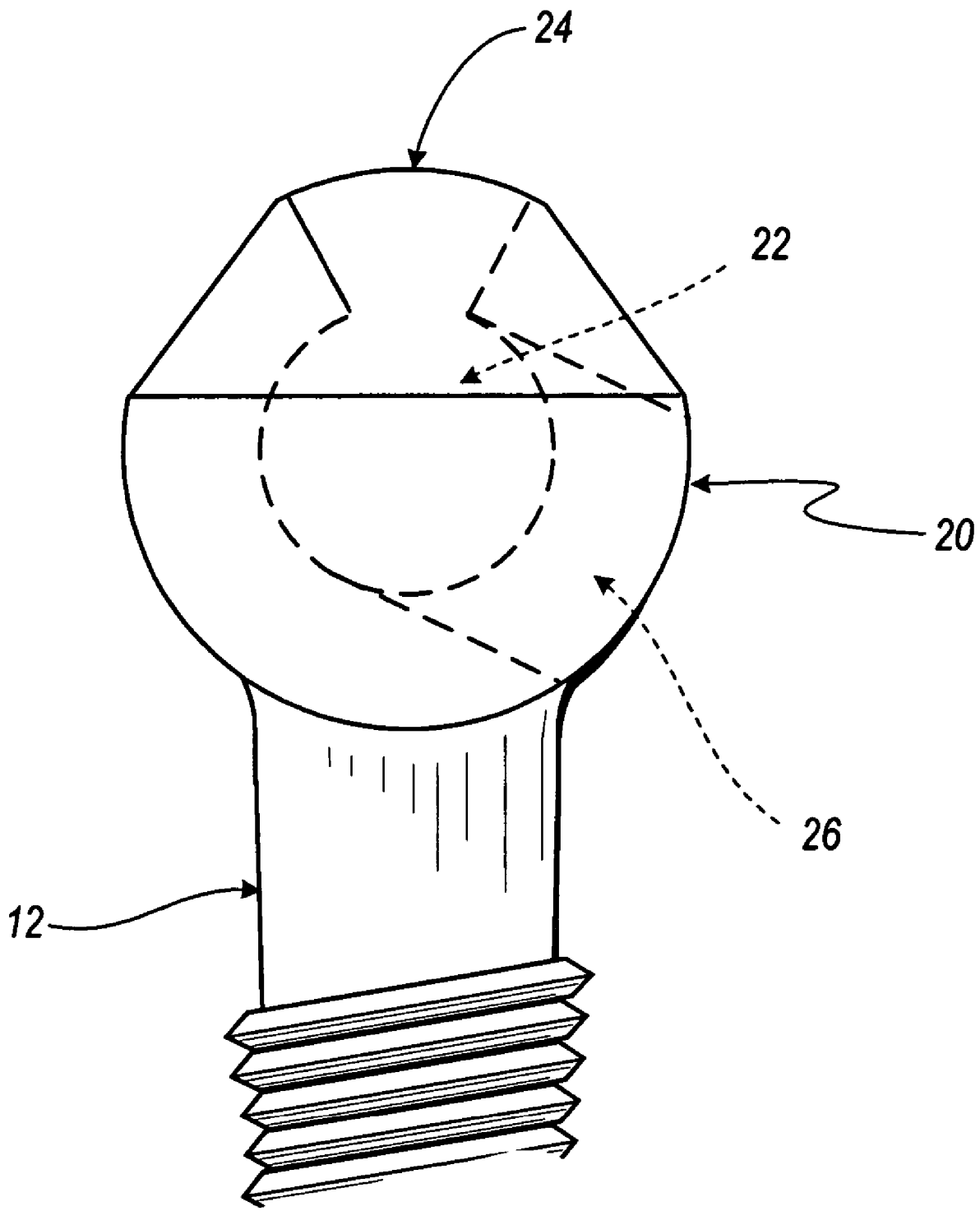
FIG. 8 is an elevation view of the connector device shown in FIG. 7.

FIG. 8 shows the embodiment of the attachment device 10 of FIG. 7 in an elevation view. While FIG. 8 shows the enlarged area 20 to include a hollow core 22, a central aperture 24, and an entry channel 26, it is noted that conical-shaped enlarged area 20 shown in FIGS. 7 and 8 may be used with any alternative embodiments of the attachment device 10 related to the method of insertion of the tension link head 34 into the hollow core 22, including, for example, the expansion slots 38, or the tension link slot 36.

In alternative embodiments not shown in the drawings, the exterior surface of the enlarged area 20 may other configurations. For example, the exterior surface of the enlarged area 20 may be formed as a polyhedron, such as a dodecahedron, or be provided with facets. In this embodiment, the head receptacle 42 of the connector 40 will also have a corresponding geometry. In this way, a polyaxial relationship is provided between the attachment device 10 and the connector 40, yet limiting this polyaxial relationship to a finite number of angular displacement.

The enlarged area 20 is shown in the drawings as at least approximately spheric. It is noted, however that the enlarged area 20 and/or the head receptacle 42 of the connector 40 may also be aspheric. The use of the aspheric construction of either the enlarged area 20 or the head receptacle 42, or both, may accommodate the elasticity and deformation of the material the structure. The amount of asphericity may be selected to control the area of surface contact between the enlarged area 20 and the head receptacle 42 of the connector 40. The amount of asphericity may also be selected to control or vary the degree of freedom required by the linkage.

Further, in any embodiment or configuration of the enlarged area 20, the external surface of the enlarged area 20 may be textured, i.e., provided with a specified surface roughness. The texture, or surface roughness, of the enlarged area 20 may be selected to properly control the friction between the enlarged area 20 and the head receptacle 42, and thus controlling, among other things, the tension force required to secure the devices together or degrees of freedom in their combination. It should be noted that the internal wall of the hollow core 22, the head end 34 of the tension link 28, and/or the head receptacle 42 of the connector 40 may also be provided with a texture, or surface roughness.

Figure 9B:
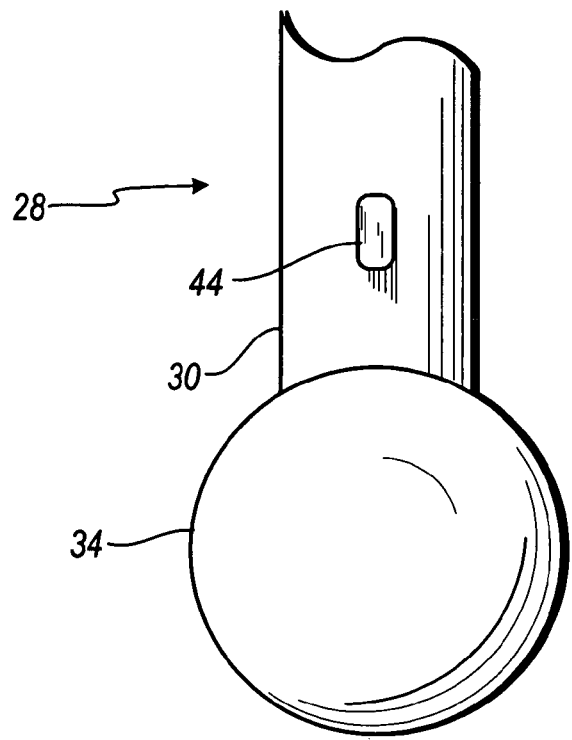
Figure 9A:
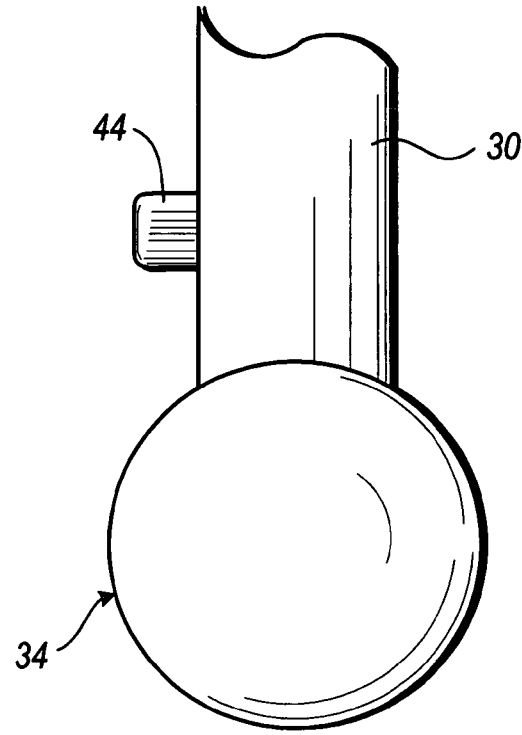
FIG. 9a is an front elevation view of one embodiment of the tension link with a link retainer of the present invention.
Figure 9C:
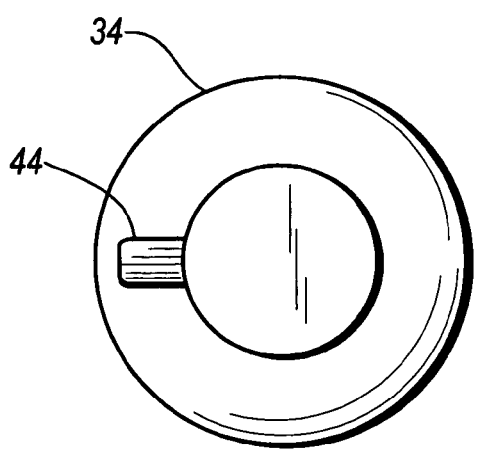

With reference to FIGS. 9a, 9b, and 9c, a tension link 28 is shown. The tension link 28 is generally a shaft 30 with a head end 34 and a thread end 32. As shown in FIGS. 9a, 9b, and 9c, one embodiment of the tension link 28 may include a link retainer 44. The link retainer 44, in this embodiment, comprises a projection on the shaft 30 of the tension link 28. The link retainer 44 may be used to prevent unwanted rotation, but not angular orientation, of the tension link 28 within the hollow core 22 of the attachment device 10.

FIG. 9a shows an embodiment of the tension link with a link retainer 44 in partial side elevation. FIG. 9b shows the same embodiment in front elevation. FIG. 9c shows this embodiment in plan view as seen from the thread end 32 of the tension link 28. The thread end 28 of the tension link 28 is not shown in FIGS. 9a, 9b, and 9c.

Figure 10A:
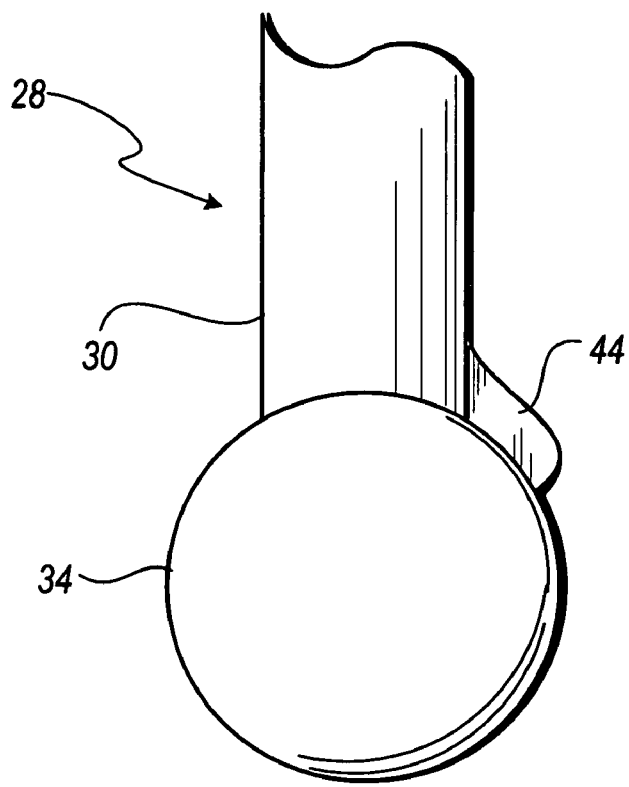
FIG. 10a is an front elevation view of an alternative embodiment of the tension link with a link retainer of the present invention.
Figure 10B:
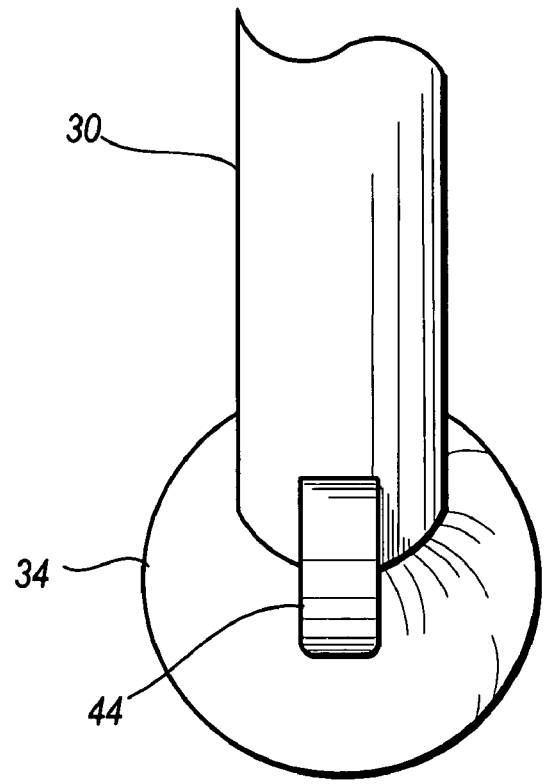

With reference to FIGS. 10a and 10b, an alternative embodiment of the link retainer 44 of the tension link 28 is shown. The tension link 28 is shown in partial side elevation and partial front elevation, in FIG. 10a and FIG. 10b, respectively. Again, this view is "partial" because the thread end 32 of the tension link 28 is omitted from the drawing. The link retainer 44 in this embodiment is a projection that spans the intersection of the shaft 30 and the head end 34 of the tension link 28 and extends partially along the surface of the head end 34. This embodiment may be used in conjunction with the embodiment of the attachment device 10 including the tension link slot 36, as shown in FIGS. 4 and 5 above. As in the previous embodiment, the tension link may be prevented from unwanted rotation of the tension link 28 within the hollow core 22. The link retainer 44 may be placed in contact with the wall of the tension link slot 36 to prevent such rotation.

Figure 11:
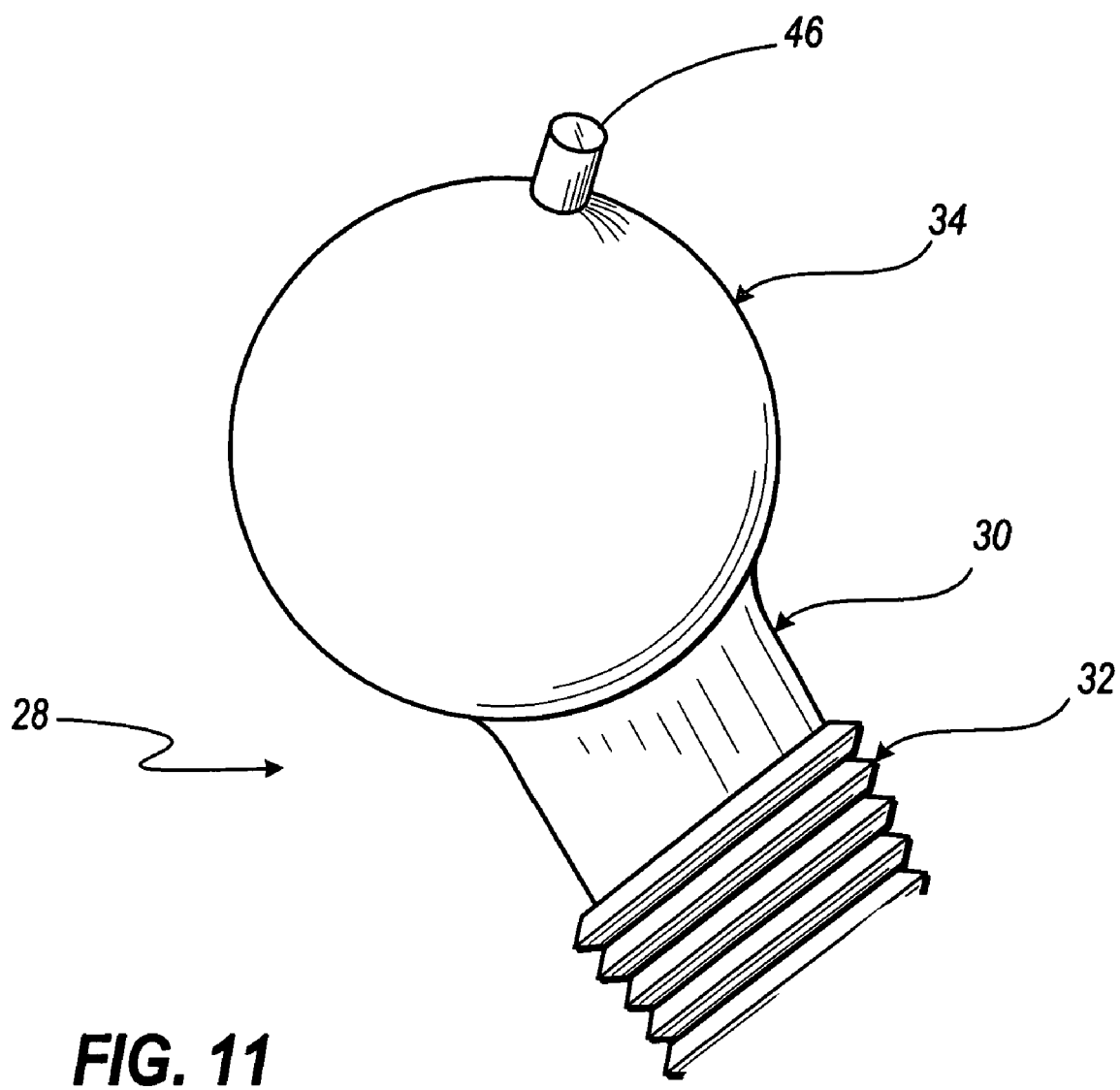
FIG. 11 is a perspective view of the tension link with head end process of the present invention.

With reference to FIG. 11, an alternative embodiment of the tension link 28 is shown. The tension link 28 again includes a shaft 30 with a head end 34 and a thread end 32, and, in this embodiment, a head end process 46. The head end process 46 is a projection on the head end 34 of the tension link 28. The head end process 46 may be used to prevent rotation of the tension link 28 within the hollow core 22 similar to the link retainer 44. However, this embodiment would most commonly be used with an attachment device 10 having a entry channel 26, and the head end process 46 could be placed in contact with a wall of the entry channel 26 to prevent the rotation.

Figure 12:
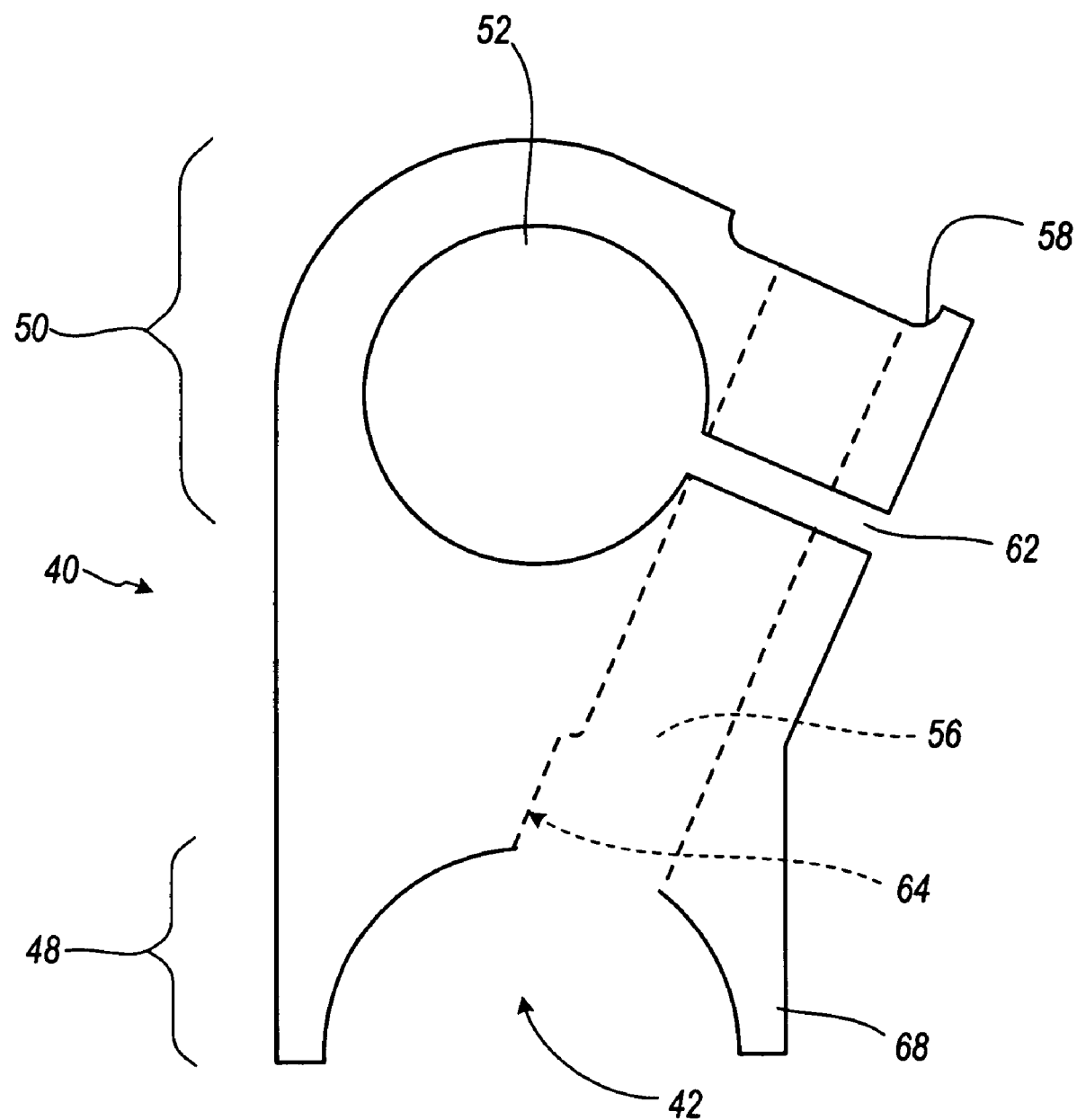
FIG. 12 is a side elevation view of one embodiment of the connector of the present invention.

With reference to FIG. 12, an embodiment of the connector 40 is shown. The connector has a receiving end 48 and a rod end 50. The receiving end 48 includes a head receptacle 42 for receiving the enlarged area 20 of the attachment device 10. The rod end 50 includes a rod aperture 52 for receiving a implant component 54, such as a spinal rod implant or other device. A tension link cavity 56 is provided from the head receptacle 42 to the rod end 50. The tension link cavity 56 is sized to allow the insertion of the thread end 32 of a tension link 28 through the connector 40. In the embodiment of the connector 40 shown in FIG. 12, a link nut recess 58 is provided at the rod end 50 adjacent to the tension link cavity 56 for seating a link nut 60 used to secure the connector 40 to the tension link 28. As shown in FIG. 12, the connector may include a gap 62 located medially between the receiving end 48 and the rod end 50, and in operative relationship with the rod aperture 52 such that when the gap 62 is closed, the rod aperture 52 may secure the implant component 54. In this embodiment, tightening of the link nut 60 on the tension link 28 closes the gap 62, and thus secures the implant component 54, concurrently with securing the connector 40 to the attachment device 10 in a desired position. The embodiment shown in FIG. 12 includes the alternative feature of a link retainer recess 64. The link retainer recess 64 is a void located along the tension link cavity 56 and adjacent to the head receptacle 42. The link retainer recess 64 accommodates the link retainer 44 of the embodiment shown in FIG. 9a, 9b and 9c, such that the link retainer 44 may contact the wall of the link retainer recess 64 and prevent undesired rotation of the tension link 28. The link retainer recess 64 should be sized accordingly.

Figure 13:
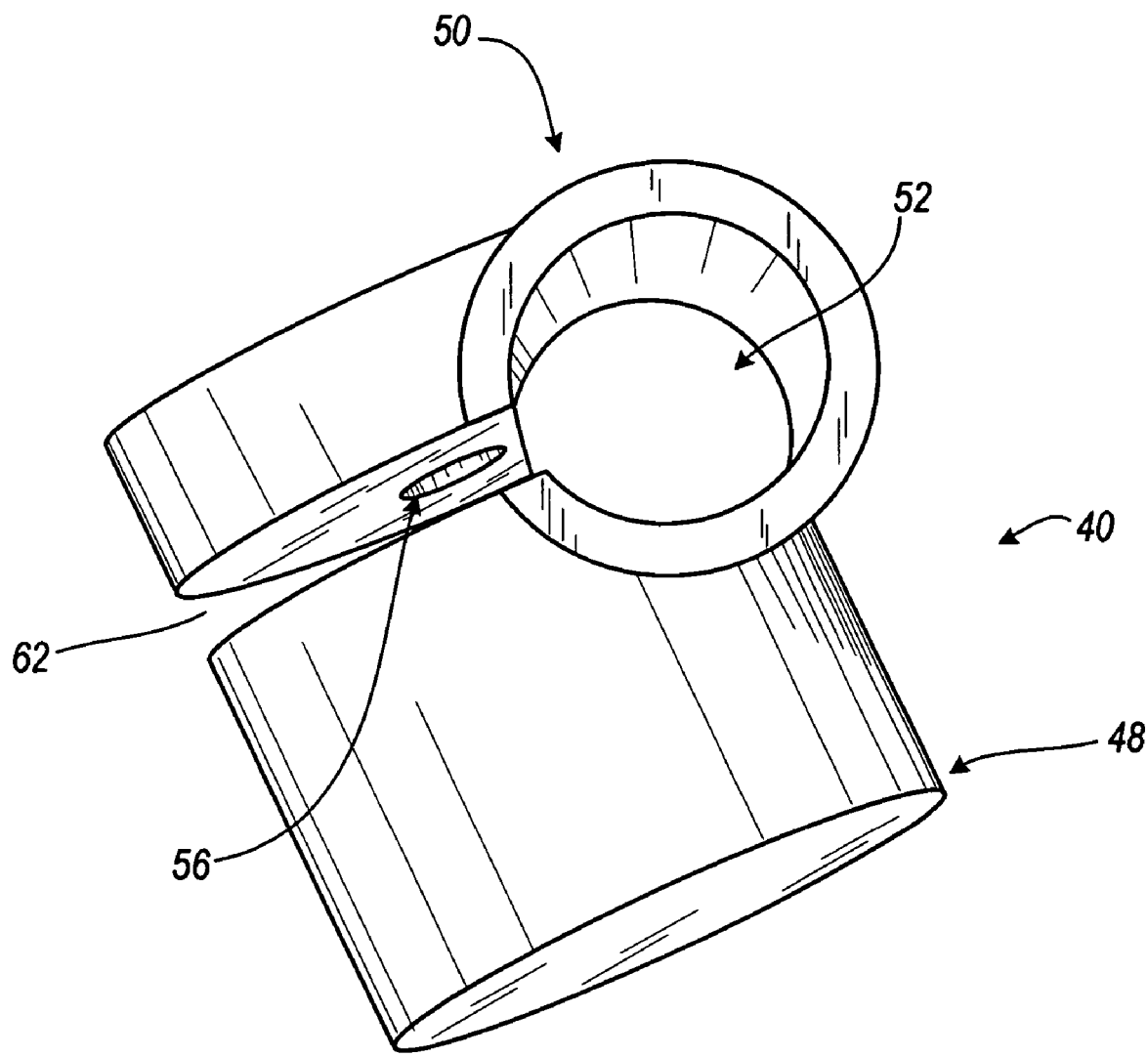
FIG. 13 is a side perspective view of an alternative embodiment of the connector of the present invention.

Referring now to FIG. 13, an alternative embodiment of the connector 40 of the present invention is shown. Like the embodiment of FIG. 13, the connector 40 of this embodiment has a receiving end 48 with a head receptacle 42, a rod end 50 with a rod aperture 52, and a tension link cavity 56. In this embodiment, however, the rod aperture 52 is offset from the body of the connector 40. The ability to offset the rod aperture 52 may provide greater latitude to the surgeon when attempting to avoid obstacles such as bones or other tissues.

Figure 14:
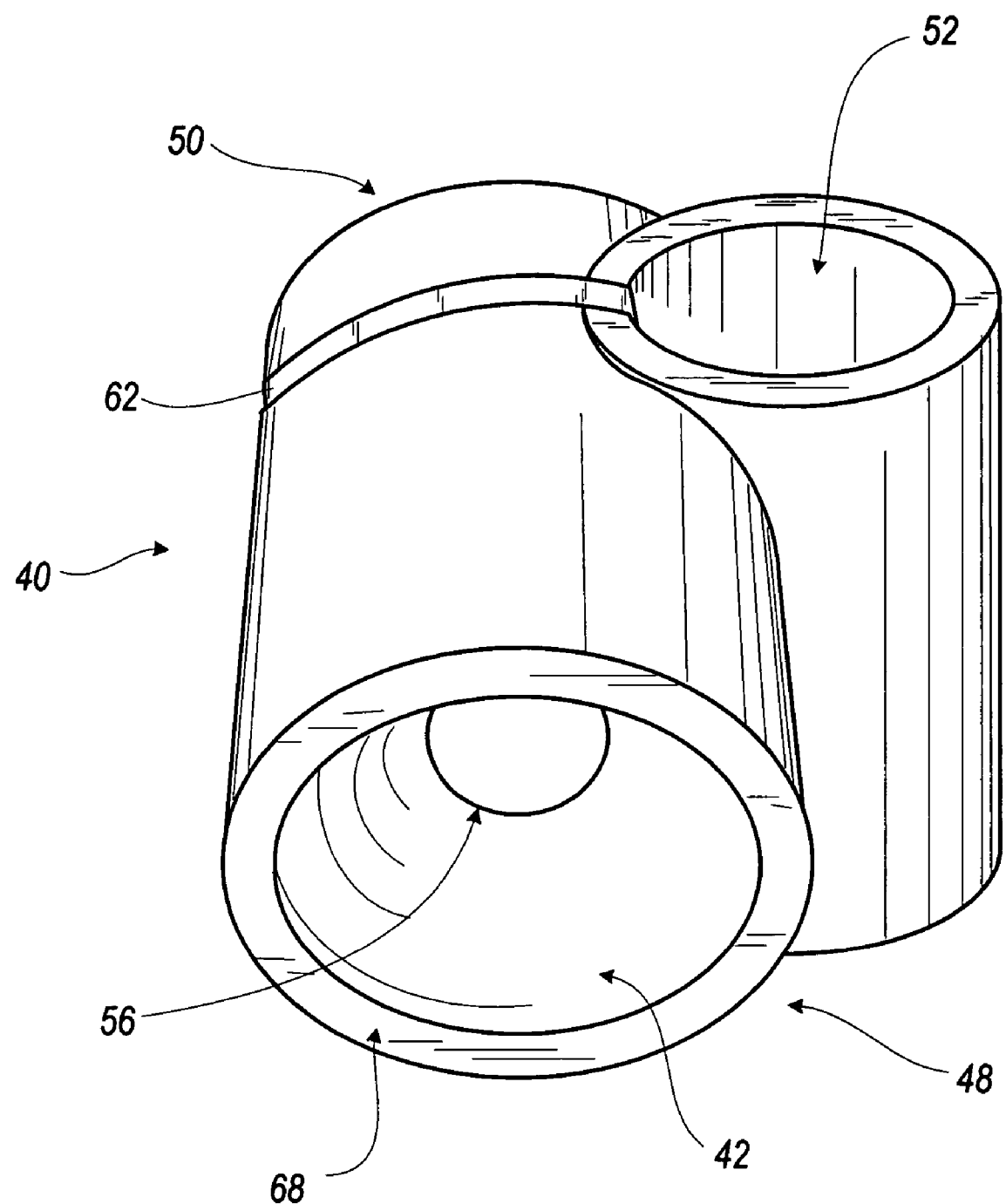
FIG. 14 is an bottom perspective view of the connector shown in FIG. 11.

FIG. 14 shows the embodiment of the connector 40 of FIG. 13 from the receiving end 48. The tension link cavity 56 in this embodiment does not include the alternative element of the link retainer recess 64.

Figure 15:
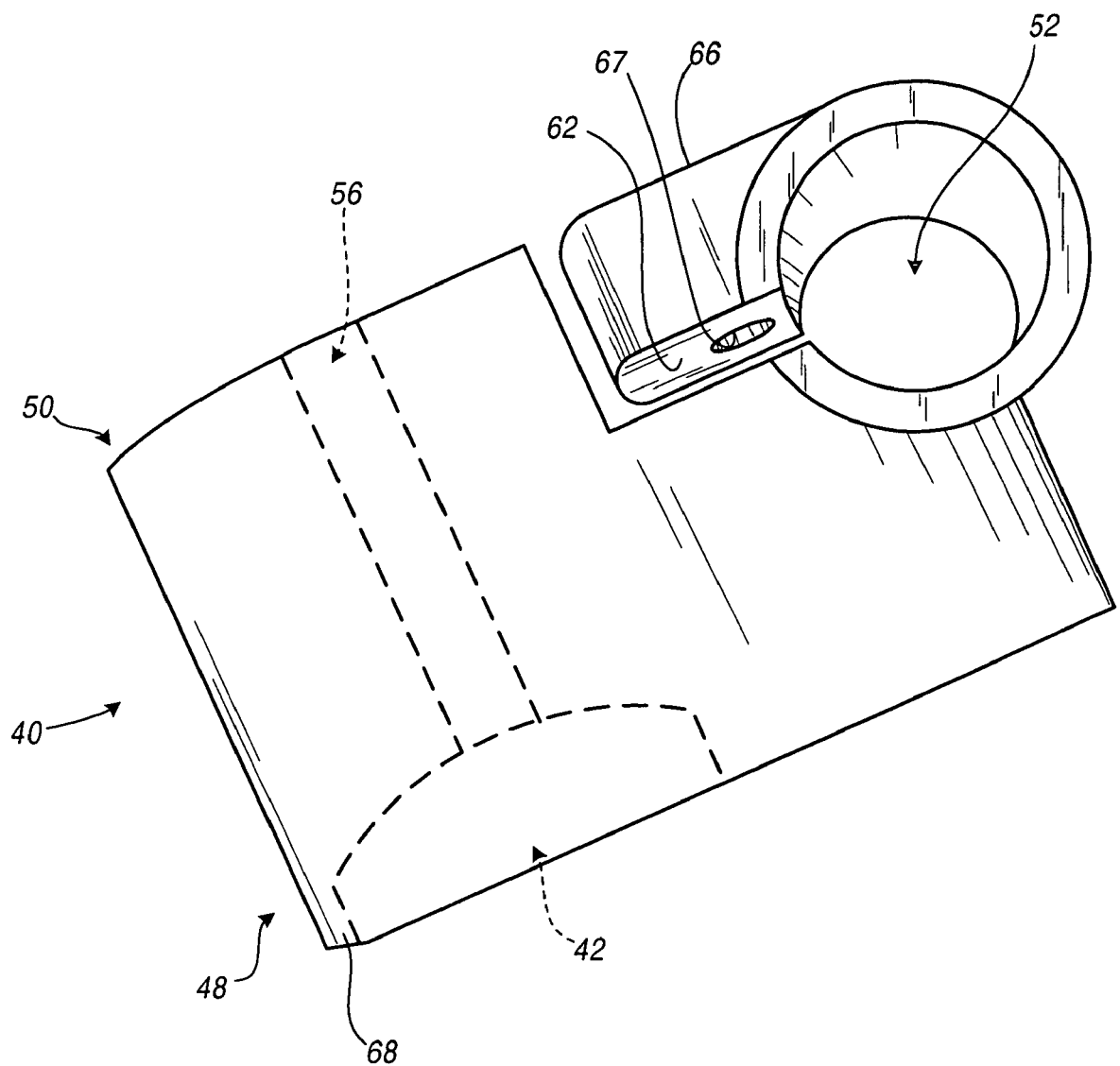
FIG. 15 is a side perspective view of another alternative embodiment of the connector of the present invention.

With reference to FIG. 15, an alternative embodiment of the connector 40 is shown. In this embodiment, the implant component 54 is secured in the rod aperture 52 separately from securing the connector 40 to the attachment device 10 by the tension link 28. The tension link cavity 56 does not intersect the gap 62 in the wall of the rod aperture 52. Instead, a portion of the wall of the rod aperture forms a tab 66 with a implant securement hole 67. The tab 66 may be secured to the connector 40 by a implant securement screw 69 inserted through the implant securement hole 67 and into the connector 40. This configuration may provide further offset capacity for the connector from the attachment device 10.

Figure 16:
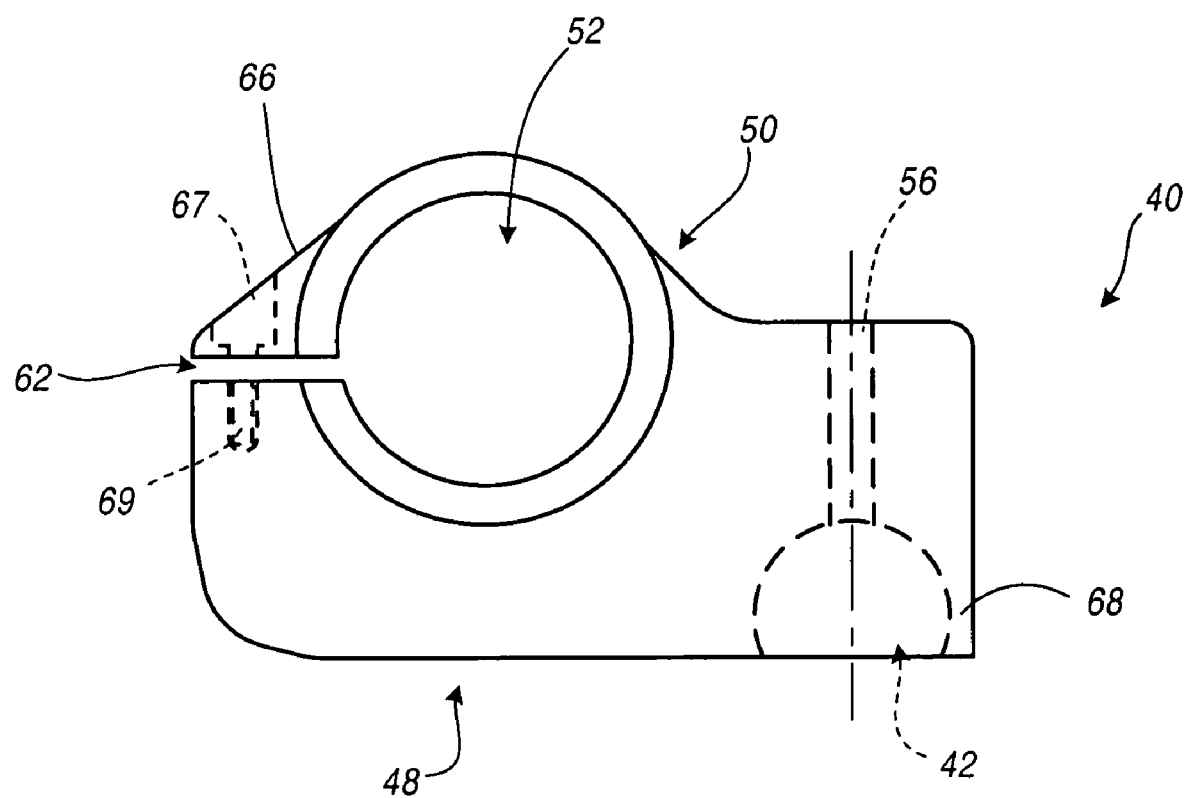
FIG. 16 is a side elevation view of yet another alternative embodiment of the connector of the present invention.

Referring now to FIG. 16, a further embodiment of the connector 40 is provided wherein the implant component 54 is secured in the rod aperture 52 separately from securing the connector 40 to the attachment device 10. As in the embodiment of FIG. 15, a portion of the wall of the rod aperture forms a tab 66 with a implant securement hole 67. The tab 66 may be secured to the connector 40 by a implant securement screw 69 inserted through the implant securement hole 67 and into the connector 40. However, in this embodiment, the tab 66 is located toward the exterior of the connector 40.

Figure 17:
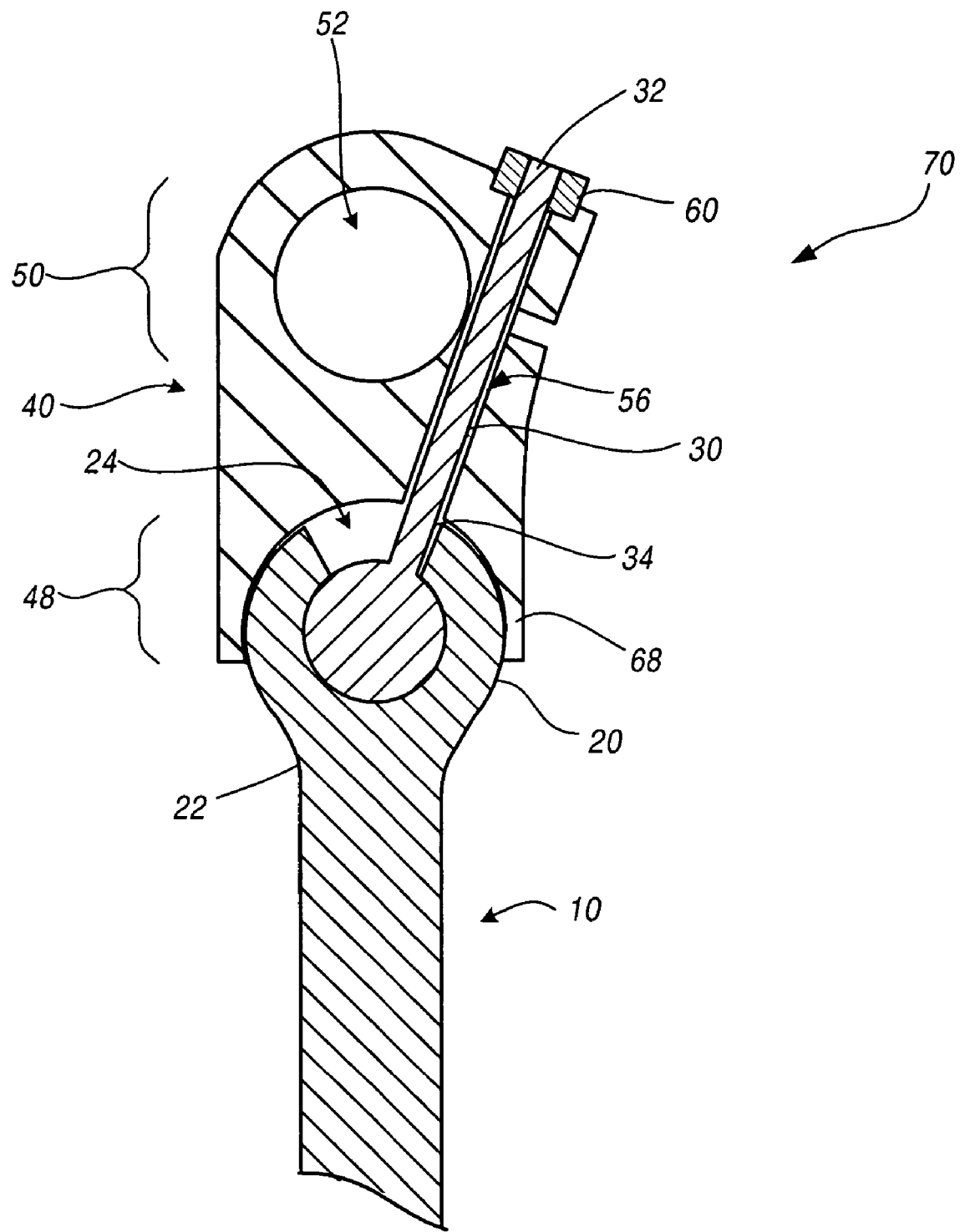
FIG. 17 is a cross-sectional view of one embodiment of the surgical implant assembly of the present invention.

With reference to FIG. 17, a possible combination of the above described elements is provided to show a surgical implantation system. The surgical implant system 70 includes a attachment device 10, a tension link 28, a connector 40, and a link nut 60. The implant component 54 is omitted from this drawing. The tension link head end 34 is inserted into the hollow core 22 of the attachment device 10. The tension link 28 extends through the tension link cavity 56 of the connector 40 such that the enlarged area 20 of the attachment device 10 is received into the head receptacle 42 of the connector 40. The connector 40 may then be secured to the attachment device 10 in proper position by tightening the link nut 60 on the tension link 28. In this embodiment, tightening the link nut 60 will also close the rod aperture gap 62 and secure the implant component 54 within the rod aperture 52.

As an aside, the head receptacle wall 68 is shown extending to approximately the "equator" or diameter of the enlarged area 20 of the attachment device 10. It should be noted that the extent that the head receptacle wall 68 engages the enlarged area 20 may be varied. For instance, a smaller wall 68 engagement may be desirable to increase the polyaxial adjustment of the assembly. Alternatively, it may be desirable to provide greater wall 68 engagement with the enlarged area 20 to prevent unnecessary deformation of the enlarged area 20, for example when the enlarged area 20 is provided with an expansion slot 38 or a tension link slot 36. Further, if the head receptacle wall 68 is designed for engagement beyond the "equator" of the enlarged area, the head receptacle wall 68 may match the contour of the enlarged area 20. In other words, the size of the head receptacle 42, at the farthest point on the receiving end 48 of the connector 40, may be smaller than the maximum size of the enlarged area 20 at its "equator." This may provide an additional advantage to the surgeon. In this situation, a tactile or audible signal may be provided when the enlarged area 20 is properly received into the head receptacle 42.

Figure 18:
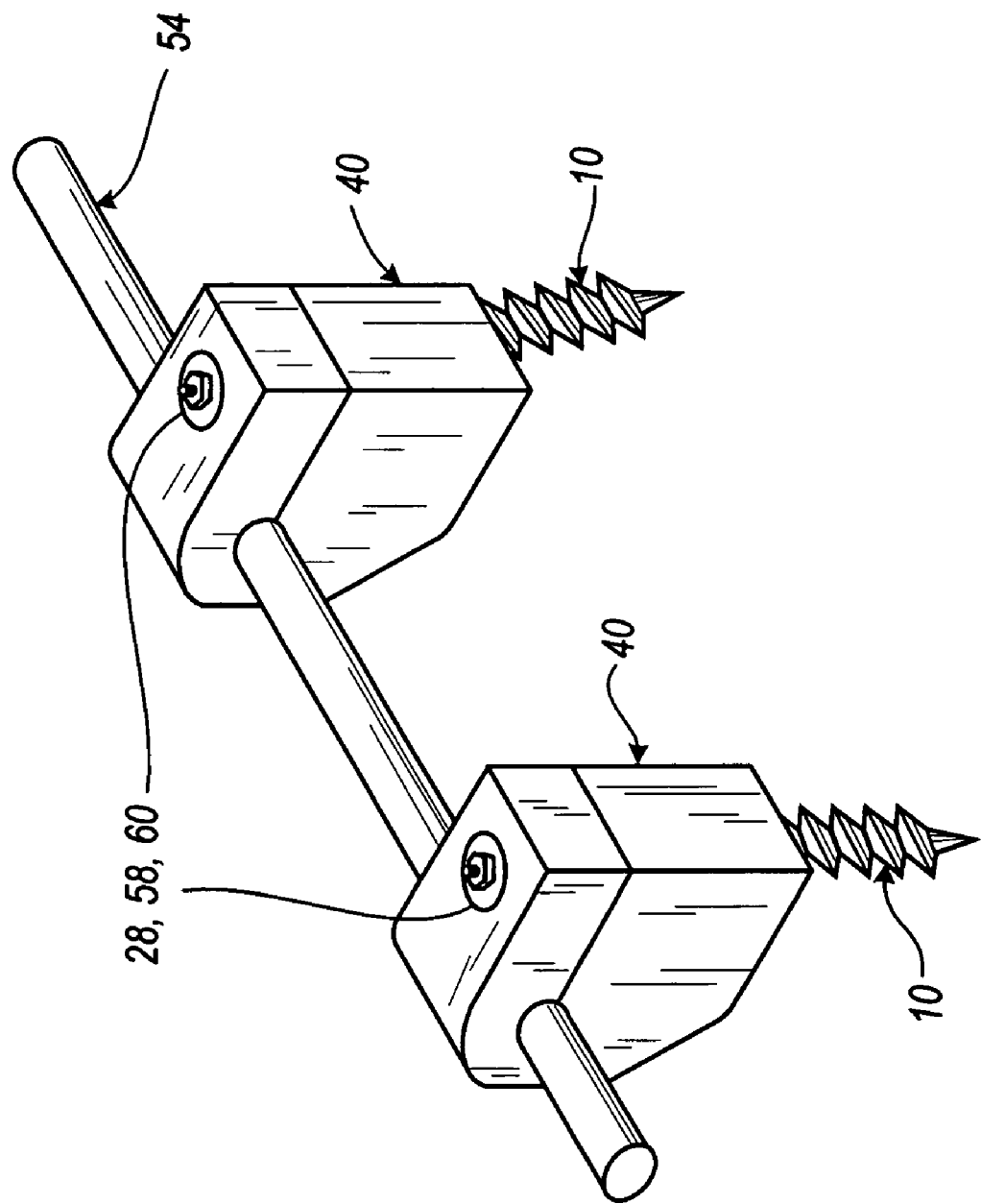
FIG. 18 is a perspective view of an alternative embodiment of the surgical implant assembly of the present invention.

With reference to FIG. 18, an alternative arrangement of the surgical implant system 70 is shown. In this embodiment, the connectors 40 secure a implant component 54, in this case a rod, to the attachment devices 10. The orientation of the attachment devices 10 illustrate the polyaxial nature of the system 70. The attachment devices may be secured to whatever structure is necessary at different angles and on different planes.

Figure 19B:
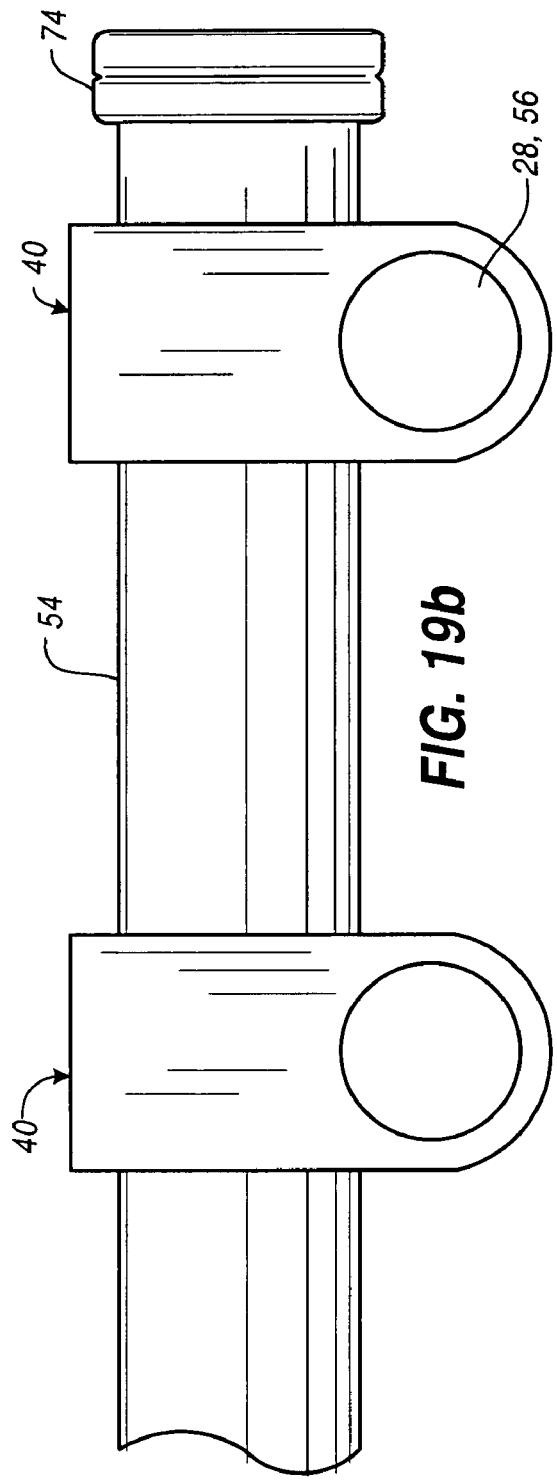
Figure 19A:
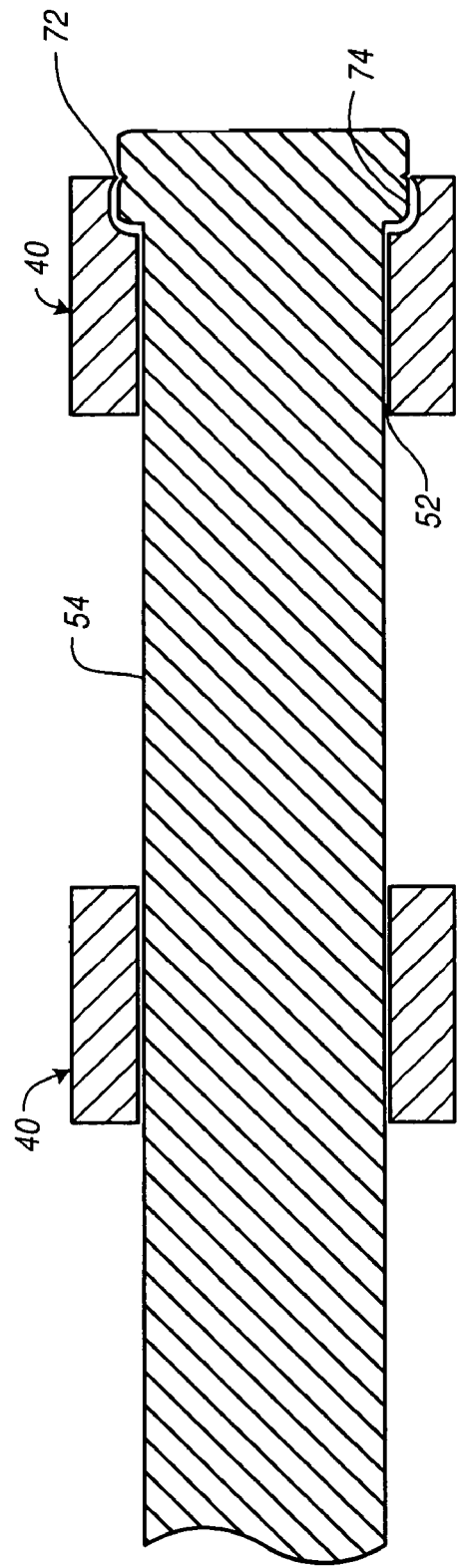
FIG. 19a is a cross-sectional elevation view of another alternative embodiment of the surgical implant assembly of the present invention.

Referring now to FIGS. 19a and 19b, an alternative embodiment of the surgical implantation system 70 is provided. In this embodiment, a dynamic system is created wherein the implant component 54 is allowed to move freely along its longitudinal axis within connector rod aperture 52. This is accomplished by manufacturing some clearance tolerance within the rod aperture 52 when the link nut 60 is completely tightened on tension link 28. FIG. 19a also shows an alternative embodiment of a retaining recess 72 adjacent to the connector rod aperture 52. The retaining recess 72 corresponds with a retaining process 74 on the implant component 54 to limit the extent of dynamic nature within the implant. The retaining recess 72 and the retaining process 74 are sized and work in relation to one another such that the longitudinal movement of the implant component 54 is arrested when the retaining process 74 nests in the retaining recess 72.

Although it is not shown in the drawings, it is also possible to use the retaining process 74 without the retaining recess 72. It this aspect, the longitudinal movement of the implant component 54 is arrested when the retaining process 74 contacts the exterior surface of the connector 40 at the rod aperture 52. It is also possible to use either of the two above embodiments on either side of the rod aperture 52, wherein the longitudinal movement of the implant component 54 can be constrained in one or both directions.

Additional embodiments of the present invention are not shown in the drawings. For example, it is expected that the attachment device 10 may be used in conjunction with a hook in place of the tension link 28. In this embodiment, the hook would have a ball end and a hook end. The ball end would be inserted into the central core 22 of the attachment device 10 and the hook end would be used to secure some bodily structure, such as a bone. The hook rod would be capable of polyaxial movement.

The present invention also relates to a method of using the embodiments as set forth above. In one embodiment, the method using a surgical implant system 70 would first require the selective insertion of the attachment device 10 into a human bone. The tension link head end 34 could then inserted into the hollow core 22 of the attachment device 10. The step of insertion of the head end 34 would depend upon the embodiment of the attachment device 10 selected. For example, if a attachment device 10 with an entry channel 26, but no tension link slot 36, is provided, the tension link 28 is positioned in the aperture 24 by way of the entry channel 26. The connector 40 is positioned on the tension link 28 by inserting the tension link 28 through the connector tension link cavity 56.

At this point, the surgeon can position the connector 40 such that the implant component 54, when properly inserted in connector rod aperture 52, is held in the desired position along the spinal column. The surgeon can then secure the position of the implant component 54 and the connector 40 in relation to the attachment device 10 by tightening the link nut 60 on the tension link threaded end 32. This process is repeated, as necessary, along the spinal column at various points along the implant component 54. In this way, the surgeon has implemented the above described embodiments as a method for using the surgical implant system, for example, in repairing a degenerative spinal condition.

It is understood that the present invention has application outside the surgical implantation field. The polyaxial securing mechanism of the present invention is not limited to medical implants. The present invention, for example, could be used to secure guy wires or rods. In this application, the anchor screw could be inserted into the ground, e.g., set directly in to the soil, mounted in a concrete footing, or similar mounting. The guy wire or rod (i.e., the tension link) could then be inserted through the anchor screw and connected to the structure to be secured. The guy rod may include a turnbuckle. The turn buckle can then be adjusted to the desired tension in the guy rod. In this way, some room for error in the location of the anchor bolt is built into the installation process. The guy rod may be installed between the anchor screw and the structure without placing undue stress on the guy rod, or requiring unnecessary bending of the guy rod, due to misalignment between the connection point on the structure and the anchor bolt position. This is especially beneficial when a turnbuckle is implemented in the guy rod. The polyaxial nature of the anchor screw would allow the turnbuckle to be more easily adjusted since the stress within the guy rod is limited to the axial direction of the rod, i.e., no bending stress on the turnbuckle.

This is just one example of the possible applications of the present invention outside the field of medical implants. Other applications, by no means exhaustive, may include connecting legs of a tripod to a base and mounting track lighting fixtures.

While various embodiments of the present invention have been described in detail, it is apparent that modifications and adaptations of those embodiments will occur to those skilled in the art. However, it is to be expressly understood that such modifications and adaptations are within the spirit and scope of the present invention, as set forth in the following claims.

What is claimed is:

1. An attachment device adapted for use with a tension link, the tension link including a tension link head and shaft, the device comprising:
a shank having first and second ends,
said first end having a securing mechanism, and
said second end devoid of threads and comprising at least a wall defined by a hollow core, a first expansion slot disposed on said wall, and a central aperture, wherein said wall includes a curved exterior surface, wherein said second end is expandably deformable to accommodate the insertion of the tension link head through the central aperture and into said hollow core, and wherein the tension link head is retained within said hollow core after insertion therein;
wherein said attachment device receivingly accepts a connector, said connector comprising a head receptacle that at least partially surrounds said second end when said connector is seated on said attachment device, said head receptacle having a curved surface for engaging the curved exterior surface of the second end when the connector is seated on the attachment device, wherein when the tension link head is inserted in the hollow core and the connector is seated on the attachment device, said head receptacle limits the deformation of the second end when a tensile force is applied through the tension link, thereby securing the tension link head within the hollow core, said tensile force operating to secure the connector to the attachment device.

2. A method of installing a surgical implant assembly, comprising the steps of:
a) securing an attachment device to human bone, said attachment device having a shank with first and second ends, said second end having a wall defined by a hollow core, a central aperture, and an expansion slot disposed on said wall through said second end to said hollow core;
b) inserting a tension link including a proximal end having a tension link head and a distal end having threads, into said attachment device by expanding said second end of said attachment device and placing said tension link head within said hollow core such that said distal end of said tension link extends through said central aperture;
c) seating a connector onto at least a portion of said second end of said attachment device, wherein said distal end of said tension link extends through a tension link cavity in said connector, further wherein said connector includes a head receptacle to receive said at least a portion of said second end of said attachment device during said seating step;
d) inserting an implant component through an aperture in said connector; and
e) securing said connector to said attachment device, and said implant component to said connector by threading and tightening a link nut onto said distal end of said tension link;
wherein, said head receptacle of said receptacle acts to partially confine said second end of said attachment device and limits expansion of said second end after said securing step.

3. The method as claimed in claim 2, wherein during step (e), tightening the link nut causes a closing of a gap, the closing of the gap causing the implant component to be secured within the aperture.

4. A surgical implant assembly, comprising:
an attachment device having first and second ends, said second end comprising an enlarged area including a wall defined by a hollow core, a central aperture contiguous with said hollow core, and at least one expansion slot disposed on said wall, wherein said wall includes a curved exterior surface;

a tension link having a proximal end and a distal end, said proximal end having a tension link head and said distal end including means for securing, said tension link head insertable into said hollow core through said central aperture by deforming said enlarged area using said expansion slot, the tension link head thereby retained within said hollow core; and a connector having a head receptacle and a tension link cavity, said head receptacle having a curved surface for engaging the curved exterior surface of the second end when the connector is seated on the attachment device, wherein when the tension link head is inserted in the hollow core and the connector is seated on the attachment device, said head receptacle limits the deformation of the second end when a tensile force is applied through the tension link, thereby securing the tension link head within the hollow core, said tensile force being applied by the securing means and operating to secure the connector to the attachment device.

5. The surgical implant assembly as claimed in claim 4, wherein said means for securing comprises a link nut threaded onto said distal end of said tension link.

6. The surgical implant assembly as claimed in claim 4, further comprising at least a second expansion slot.

7. The surgical implant assembly as claimed in claim 6, wherein said second expansion slot is positioned substantially diametrically opposite said at least one expansion slot.

8. The surgical implant assembly as claimed in claim 4, wherein said second end is devoid of threads.

9. The surgical implant assembly as claimed in claim 4, wherein said first end of said attachment device comprises screw threads.

10. The attachment device as claimed in claim 4, wherein said connector further comprises a gap provided in association with an implant component aperture, wherein when an implant component is inserted in said implant component aperture, said tension additionally operates to close said gap to thereby secure said implant component in said implant component aperture.

11. An attachment device adapted for use with a tension link, the tension link including a tension link head and shaft, the device comprising:
   a shank having first and second ends,
   said first end having a securing mechanism, and
   said second end devoid of threads and comprising at least a wall defined by a hollow core, a first expansion slot disposed on said wall, and a central aperture, wherein said wall includes a curved exterior surface, wherein said second end is expandably deformable to accommodate the insertion of the tension link head through the central aperture and into said hollow core, and wherein the tension link head is retained within said hollow core after insertion therein;
   wherein said attachment device receivingly accepts a connector, said connector comprising a head receptacle that at least partially surrounds said second end when said connector is seated on said attachment device, said head receptacle having a curved surface for engaging the curved exterior surface of the second end when the connector is seated on the attachment device, wherein when the tension link head is inserted in the hollow core and the connector is seated on the attachment device, said head receptacle limits the deformation of the second end when a tensile force is applied through the tension link, thereby securing the tension link head within the hollow core, said tensile force operating to secure the connector to the attachment device;
   wherein said connector further comprises a gap provided in association with an implant component aperture, wherein when an implant component is inserted in said implant component aperture, said tension additionally operates to close said gap to thereby secure said implant component in said implant component aperture.

12. A surgical implant assembly, comprising:
   an attachment device having first and second ends, said second end comprising an enlarged area including a wall defined by a hollow core, a central aperture contiguous with said hollow core, wherein said wall includes a curved exterior surface;
   a tension link having a proximal end and a distal end, said proximal end having a tension link head and said distal end including means for securing, said tension link head insertable into said hollow core;
   an implant component; and
   a connector having a head receptacle provided in association with a tension link cavity, and an implant component aperture provided in association with a gap, said implant component aperture operable to receive the implant component, said head receptacle having a curved surface for engaging the curved exterior surface of the second end when the connector is seated on the attachment device, wherein the tension link head is inserted completely into the hollow core and the connector is seated on the attachment device, a tensile force applied by the securing means operates to secure the connector to the attachment device, wherein said tensile force also operates to close said gap to thereby secure the implant component within the implant component aperture, and further wherein said head receptacle limits deformation of said second end of said attachment device when said tensile force is applied.

13. The surgical implant assembly as claimed in claim 12, wherein said means for securing comprises a link nut threaded onto said distal end of said tension link.

14. The surgical implant assembly of claim 12 wherein said second end of said attachment device includes an expansion slot disposed on said wall and is deformable to accommodate the insertion of the tension link head through the central aperture and into said hollow core, and
   wherein the tension link head is retained within said hollow core by an engagement between the head receptacle and the curved exterior surface of the second end, the engagement occurring when the tension link head is inserted in the hollow core and the connector is seated on the attachment device, wherein said engagement is maintained by a tensile force applied by the securing mechanism through the tension link, and operates to limit the deformation of the second end when thereby securing the tension link head within the hollow core.

15. The surgical implant assembly as claimed in claim 14, further comprising at least a second expansion slot.

16. The surgical implant assembly as claimed in claim 15, wherein said second expansion slot is positioned substantially diametrically opposite said at least one expansion slot.

17. The surgical implant assembly as claimed in claim 12, wherein said attachment device includes entry channel operable to receive said tension link.

18. The surgical implant assembly as claimed in claim 17, wherein said attachment device includes a tension link slot.

19. The surgical implant assembly as claimed in claim 12, wherein said second end is devoid of threads.

20. The surgical implant assembly as claimed in claim 12, wherein said first end of said attachment device comprises screw threads.

* * * * *